Figure 5:
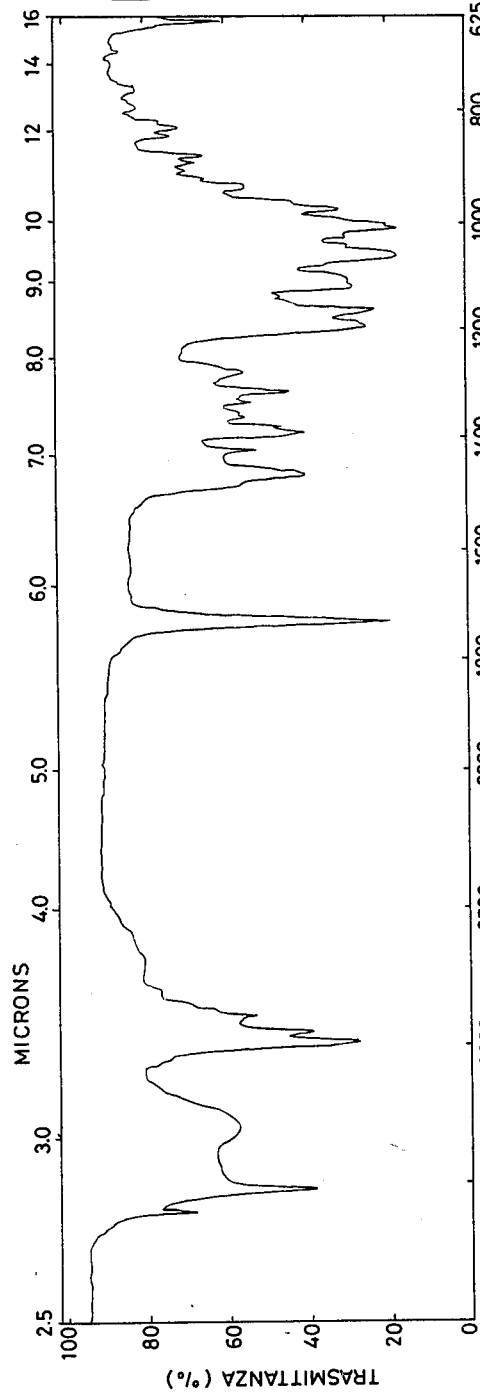

United States Patent [19]

Toscano et al.

[11] 4,439,426

[45] Mar. 27, 1984

[54] SEMISYNTHETIC MACROLIDIC ANTIBIOTICS, INTERMEDIATE COMPOUNDS FOR THEIR PREPARATION AND RELATED PHARMACEUTICAL COMPOSITIONS CONTAINING THEM

[75] Inventors: Luciano Toscano, Milan, Italy; Leonardo M. Cappelletti, Fayetteville, N.Y.

[73] Assignee: Pierrel S.p.A., Napoli, Italy

[21] Appl. No.: 338,105

[22] Filed: Jan. 8, 1982

[30] Foreign Application Priority Data

Jan. 9, 1981 [IT] Italy ............................. 19082 A/81
Nov. 27, 1981 [IT] Italy ............................. 25344 A/81
Nov. 27, 1981 [IT] Italy ............................. 25346 A/81

[51] Int. Cl.³ .................. A61K 31/71; C07D 313/00; C07H 17/08; C12P 19/62
[52] U.S. Cl. .................................. 424/181; 424/180; 435/74; 435/172; 435/253; 536/7.2; 549/264; 549/271
[58] Field of Search ............... 536/9, 7.2; 424/180, 424/181; 549/271, 264

[56] References Cited

U.S. PATENT DOCUMENTS 3,697,547 10/1972 Kurath et al. ............... 549/271
3,780,019 12/1973 Wildsmith ..................... 536/9
3,816,397 6/1974 Tadanier et al. ............. 536/9
3,855,200 12/1974 Krowicki et al. ............ 536/9

OTHER PUBLICATIONS

Bright, "Chem. Abst.", vol. 90, 1979, p. 152552(c).
Adachi et al., "Chem. Abst.", vol. 90, 1979, p. 152554(e).

Primary Examiner—Johnnie R. Brown
Attorney, Agent, or Firm—Murray and Whisenhunt

[57] ABSTRACT

From the fermentation carried out with mutants blocked in the synthesis respectively of erythromycin and of oleandomycin, namely Streptomyces erythreus ATCC 31772 and Streptomyces antibioticus ATCC 31771, using as the substrate a derivative of erythronolide A, namely (8S)-8-fluoroerythronolide A, a derivative of erythronolide B, namely (8S)-8-fluoroerythronolide B, or a derivative of 3-O-mycarosyl-erythronolide B, namely 3-O-mycarosyl-(8S)-fluoroerythronolide B, the corresponding (8S)-8-fluoro derivatives of the erythromycins A, B, C and D, as well as 3-O-oleandrosyl-5-desosaminyl-(8S)-8-fluoroerythronolide A and 3-O-oleandrosyl-5-O-desosaminyl-(8S)-8-fluoroerythronolide B, all belonging to the class of the macrolide antibiotics are obtained.

The preparation of the aforesaid substrate comprises the convention of erythronolide A, erythronolide B or 3-O-mycarosyl-erythronolide B into the corresponding hermiacetal, the reaction of the latter with a compound capable of generating electrophlic fluorine and the opening of the resulting acetal with aqueous acid.

25 Claims, 6 Drawing Figures

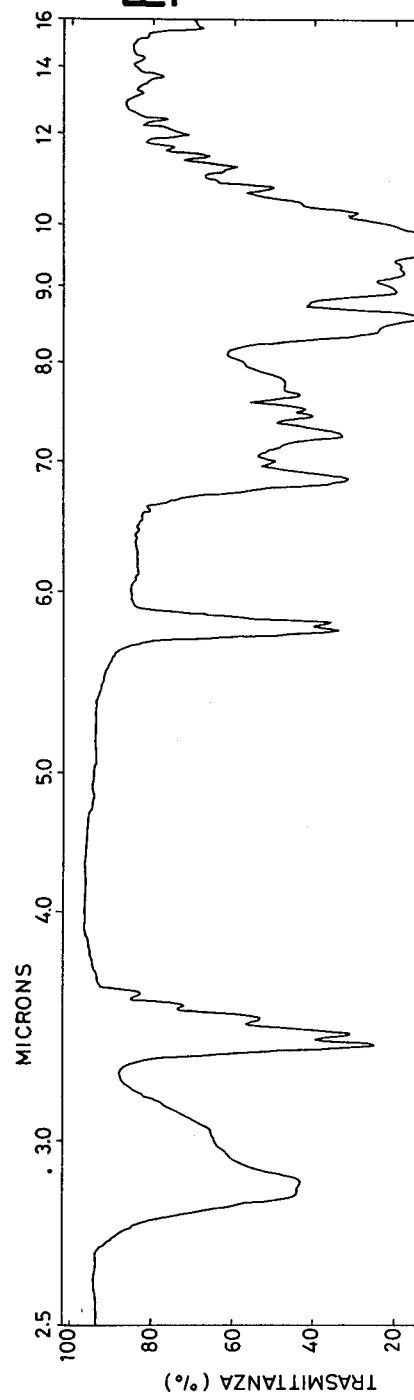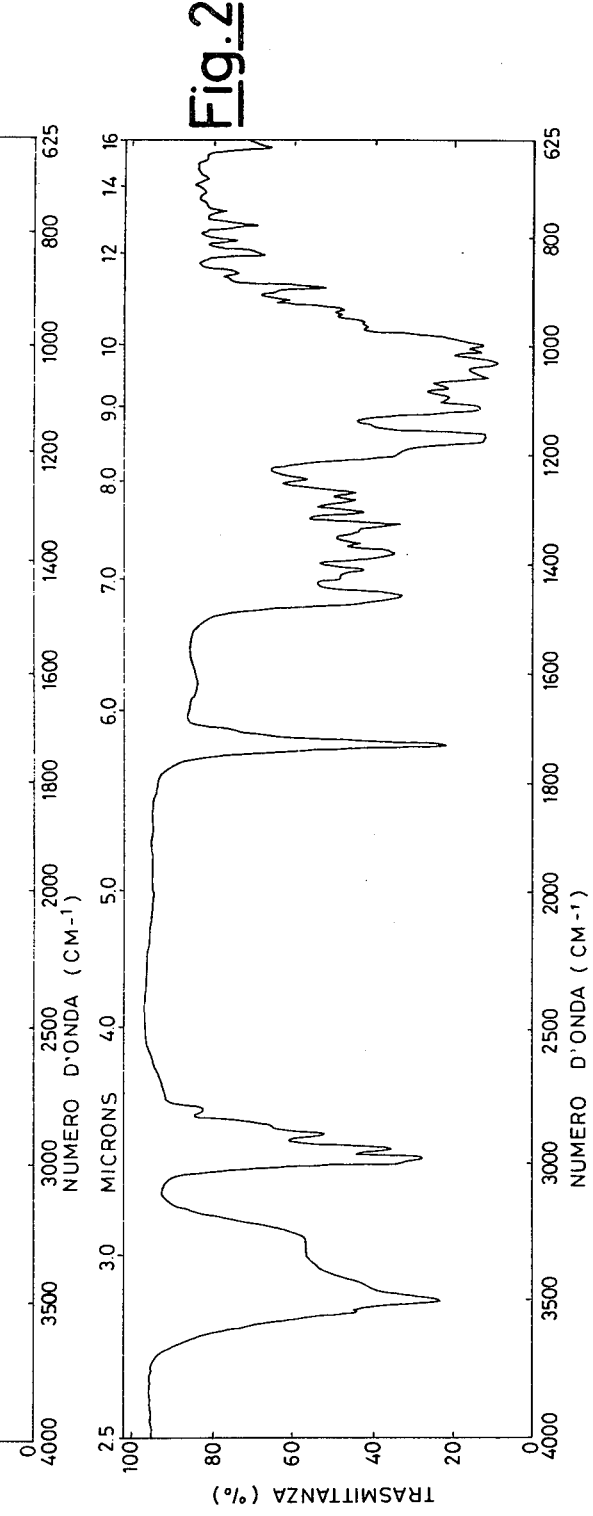

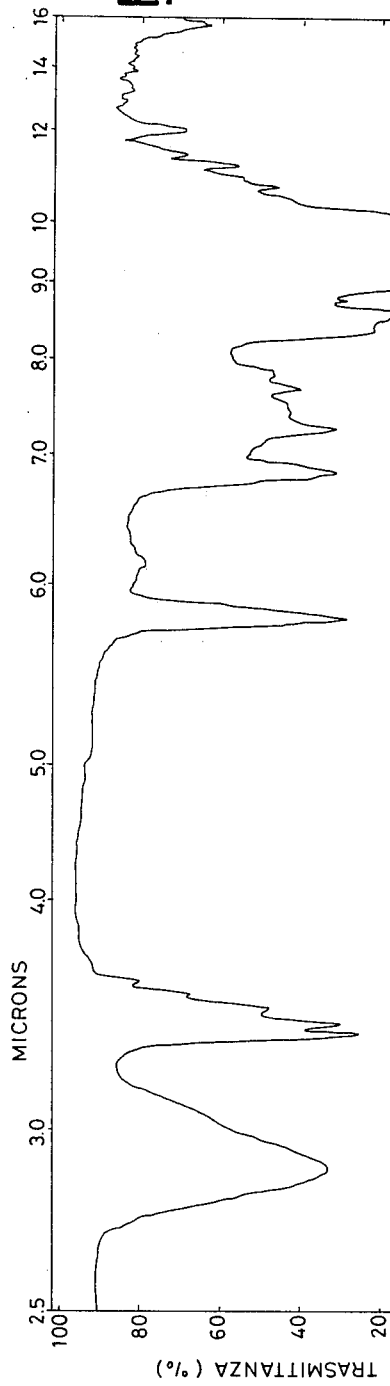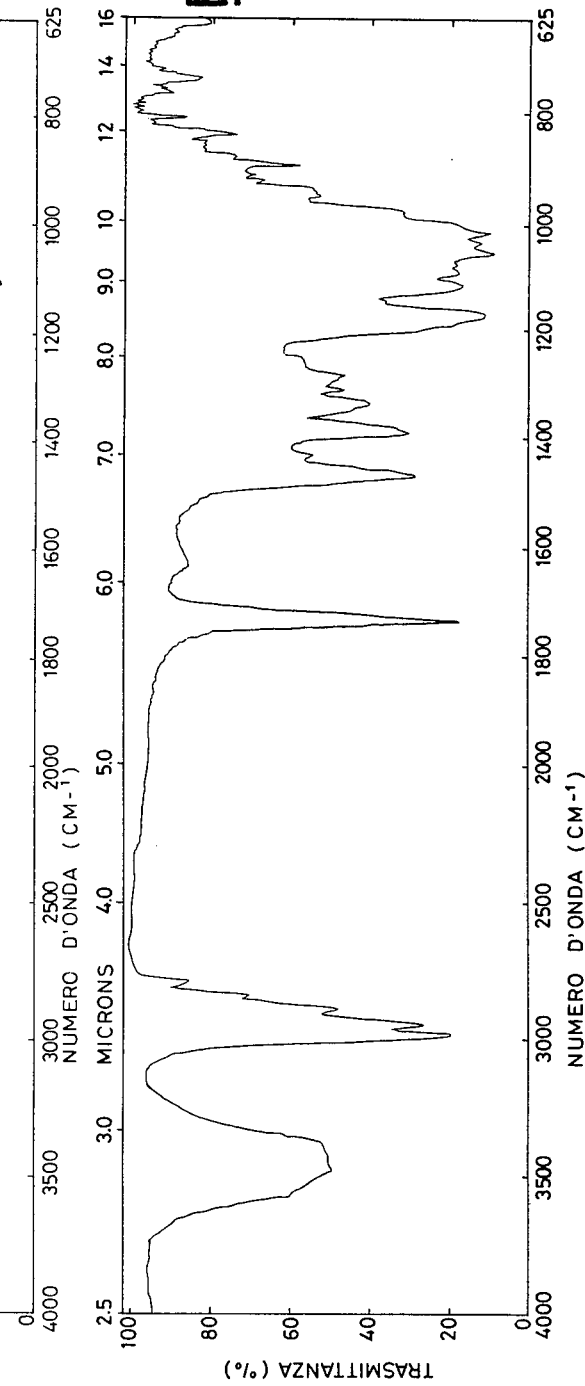

SEMISYNTHETIC MACROLIDIC ANTIBIOTICS, INTERMEDIATE COMPOUNDS FOR THEIR PREPARATION AND RELATED PHARMACEUTICAL COMPOSITIONS CONTAINING THEM

The present invention relates to novel macrolide antibiotics, useful as antibacterial agents, and a microbiological process for their production starting from a novel intermediate, derived from the erythronolide A, the erythronolide B or from the 3-O-mycarosyl-erithronolide B.

The invention relates as well to a novel micro-organism, useful for the production of the macrolide antibiotics of the invention, as well as to the related method for the preparation thereof by mutagenesis starting from a known stock.

The present invention relates furthermore to novel intermediates deriving from erythronolide A, from erythronolide B or from 3-O-mycarosyl-erythronolide B and to the related chemical syntesis process.

As previously mentioned, the novel semisynthetic macrolide antibiotics of the present invention are useful as antibacterial agents. They in fact show, in comparison with the erythromycins of known type, activity spectra and levels equal or broader, are less susceptible of being degraded in an acidic environment, whereby permit a better adsorption by oral route; their esters or salt-esters are adsorbed in a quicker and more complete manner giving place to higher and more delayed hematic levels than the free bases.

The novel antibiotics of the present invention, owing to the presence of the basic group form addition salts with acids both organic and inorganic. The aforesaid salts can be prepared from the free base by conventionally used methods for the preparation of addition salts of basic antibiotics.

The salts which are not water soluble are used in liquid oral suspension (they are little bitter). Monoester derivatives of the novel antibiotics and addition salts thereof can be prepared by methods like those used for the preparation of esters and salts-esters of erythromycin A.

The esters and salt-esters of erythromycin A and the methods for their preparation are known in the art. Examples of esters, salt-esters and salts of (8S)-8-fluoroerythomycin A (P-80206), (8S)-8-fluoroerythromycin B(P-80203), (8S)-8-fluoroerythromycin C(P-80205), (8S)-8-fluoroerythromycin D (P-80202), 3-O-oleandrosyl-5-O-desoaminyl-(8S)-8-fluoroerythronolide A(P-80207) and 3-O-oleandrosyl-5-O-desosaminyl-(8S)-8-fluoroerythronolide B (P-80204) (wherein the abbreviations in brackets indicate the own references of the Applicant), which can be prepared are acetate, propionate, butyrate, succinate, valerate, ethylsuccinate, propionate laurylsulphate, stearate, lactobionate, glucoheptonate, sulphate, laurylsulphate, carbonato-derivatives and the like, among which the lactobionate and the glucoheptonate, being water soluble salts, permit the administration by intravenous route. In turn, the ethylsuccinate permits the administration both by oral and by parenteral route.

The novel antibiotics according to the invention are white, bitter, odorless powders, temostable in the powder form, more stable than erythromycin A in water solution at acidic pH and, thus, more stable in the gastric acidic environment. The half life times of the initial activity of erythromycin A and of the macrolide antibiotics of the present invention in solution at several pH values are reported in the following table 1.

TABLE 1

Stability in acidic environnment at 25° C. of the novel antibiotics in comparison with the erythromycin A

| Erythromycin A | | | |
|---|---|---|---|
| pH | 2.0 | 3.0 | 4.0 |
| t ½ (minutes) | 2 | 6 | 120 |
| (8S)-8-fluoroerythomycin A (P-80206) | | | |
| pH | 2.0 | 3.0 | 4.0 |
| t ½ (hours) | 9 | 82.5 | 100 |
| (8S)-8-fluoroerythromicin B (P-80203) | | | |
| pH | 2.0 | 3.0 | 4.0 |
| t ½ (hours) | 3 | 45 | 100 |
| (8S)-8-fluoroerythromycin C (P-80205) | | | |
| pH | 2.0 | 3.0 | 4.0 |
| t ½ (hours) | 1.65 | 41.5 | 100 |
| (8S)-8-fluoroerythromycin D (P-80202) | | | |
| ph | 2.0 | 3.0 | 4.0 |
| t ½ (hours) | 0.4 | 10 | 100 |
| 3-O—oleandrosyl-5-O—desosaminyl-(8S)—8-fluoroerythronolide A (P-80207) | | | |
| pH | 2.0 | 3.0 | 4.0 |
| t ½ (hours) | 10 | 100 | 100 |
| 3-O—oleandrosyl-5-O—desosaminyl-(8S)—8-fluoroerythronolide B (P-80204) | | | |
| pH | 2.0 | 3.0 | 4.0 |
| t ½ (hours) | 25 | 100 | 100 |

Note: t ½ represents the time for reducing to one half the initial power of the antibiotic determined by microbiological method through diffusion on a plate using the test stock *Microccocus luteus (Sarcina lutea)* ATCC 9341.

According to a first feature of the invention, there are prepared the novel intermediates deriving from erythronolide A, erythronolide B or 3-O-mycarosylerythronolide B, which are used in the microbiological process for the preparation of the novel antibiotics.

It is well known (R. A. LeMahieu et al, J. Med. Chem. 17, 963 (1974)), that the erythronolide A is a substrate which can be obtained from erythromycin A by selective removal of the sugars cladinose and desosamine.

It is also known that the erythronolide B and the 3-O-mycarosyl-erythronolide B are substrates which can be obtained by direct fermentation in relevant amounts and thus at industrially feasible costs, using micro-organisms producers of erythromycin and their mutants. On the other hand, as it is also well known, apart from the production of normal erythromycin A, these substrates do not find use in other fermentations which may give place to antibiotics devoid of the disadvantages and problems affecting the erythromycin by itself, whereas from the industrial point of view their utilization appears mostly desirable.

It has been now found that the derivatives of erythronolide A, of the erythronolide B or of 3-O-mycarosyl-erythronolide B, which can be prepared by chemical way in a simple and industrially feasible manner, are useful substrates for fermentation processes which, making use of micro-organisms obtained by mutagenesis from the stocks adapted for the microbiological production of erythromycin A, give place to the novel macrolide antibiotics of the present invention, as it will be more specifically described hereinafter.

The chemical process for the preparation of the novel intermediates according to the present invention is represented by the following scheme:

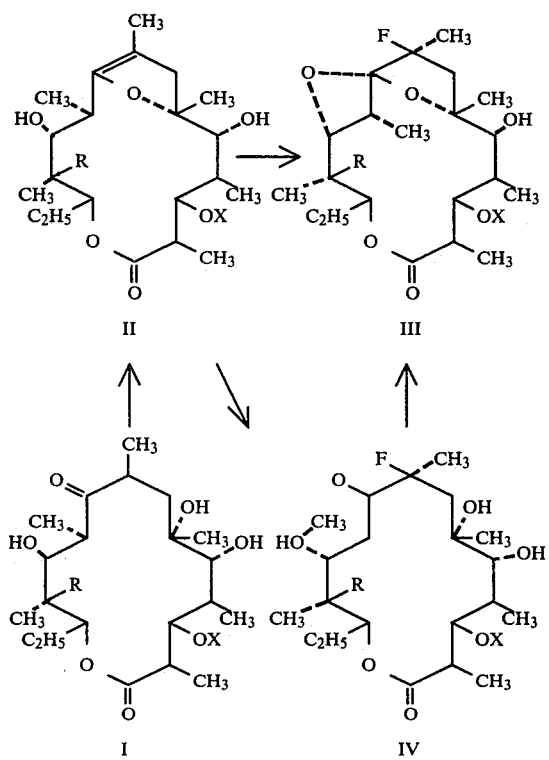

wherein when R=H, X represents H or the group:

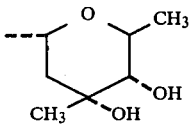

and, when R=OH, X=H, and is characterized by the steps of:

(a) treatment of a compound (I), selected among erythronolide A, erythronolide B and 3-O-mycarosyl-erythronolide B with an anhydrous acid, such as glacial acetic acid or a methanolic solution of hydroxylamine hydrochloride, to form the compound (II), namely 8,9-anhydroerythronolide A-6,9-hemiacetal, 8,9-anhydroderythronolide B-6,9-hemiacetal or 3-O-mycarosyl-8,9-anhydro-erythronolide B-6,9-hemiacetal;

(b) reaction of the compound (II) with a reagent capable of generating electrophilic fluorine, preferably selected among fluoroxy-perfluoro-alkanes (having the general formula $C_nF_{2n+1}OF$) and perchloryl fluoride, to form the corresponding acetal (III) in the presence of an inert organic solvent and at low temperature;

(c) reaction of the compound (III) with an aqueous acid whereby the desired compound (IV) is formed.

With reference to the step (b), among the reagents of the class of the fluoroxyperfluoro-alkanes that mostly used is the fluoroxy-trifluoromethane, which is commercially available.

Other reagents containing fluorine atoms having positive charge which can be used in the present reaction comprise fluoroxy-sulphur-penta-fluoride, molecular fluorine and lead tetraacetate-hydrofluoric acid.

Among the reaction solvents there are contemplated the chlorinated hydrocarbons such as trichlorofluoromethane (Freon 11), chloroform, methylene chloride and the like, tetrahydrofuran and their mixtures.

It is preferable to carry out the reaction at low temperatures, preferably in the range of between $-75°$ C. and $-85°$ C., under continuous stirring.

The reaction is normally completed in a time of between about 15 minutes and one hour.

It is important to point out that the forming of the acetal (III) is accompanied by the forming already in this step of not negligible amounts of the desidered compound (IV).

As regards the third reaction step (c), organic or mineral aqueous acids, such as acetic or hydrochloric acid, are used. For the reaction temperatures of between about 30° C. and about 150° C. can be adopted. The resulting product (IV) is recovered in purified form by means of recrystallization or chromatography.

Also the compounds (II), (III) and (IV), being novel, are part of the invention.

The invention, besides the intermediate (IV), is based on the use of the mutant, Streptomyces erythreus ATCC 31772, of blocked type, which is obtained through mutagenesis by chemical methods (namely by means of chemical mutagenic agents), by irradiation with U.V. rays, or X rays, by the action of phages and the like. The culture of the Streptomyces erythreus ATCC 31772, using the compound (IV) as the substrate leads to the production of the novel macrolide antibiotics of the class of the (8S)-8-fluorinated erythromycins (Scheme II: P-80202, P-80203, P-80205 and P-80206), respectively having $R_s$ 0.9, 1.13, 0.89, and 1.12 with respect to the erythromycin B, said antibiotics having furthermore specific colours if treated with chromatic reagents and heated, namly the first one having brick red colour (hot), the second and the fourth dark brown violet colour (after cooling), and the third dark colour (hot).

Scheme II

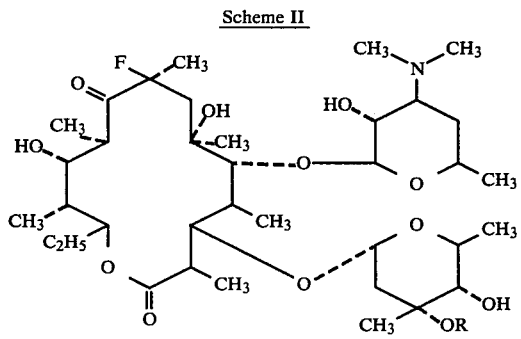

R=CH₃ (8S)-8-fluoroerythromycin B (P-80203)
R=H (8S)-8-fluoroerythromycin D (P-80202)

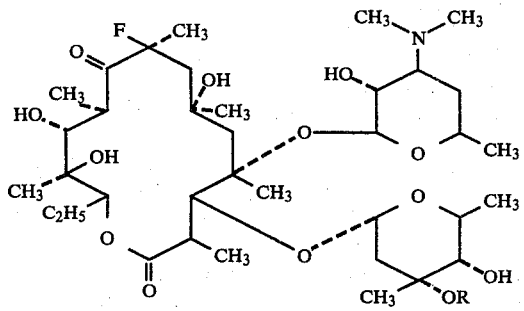

R=CH₃ (8S)-8-fluoroerythromycin A (P-80206)
R=H (8S)-8-fluoroerythromycin C(P-80205)

It is a further object of the invention a microbiological process for the preparation of novel macrolide antibiotics of the erythromycin class which is characterized in that a compound (IV) is used as the substrate for the fermentation with *Streptomyces antibioticus* ATCC 31771 which gives respectively to the antibiotic 3-O-oleandrosyl-5-O-desosaminyl-(8S)-8-fluoroerythronolide A (Scheme III: P-80207), having $R_{st}$ 0.87 with respect to the oleandomycin and 0.80 with respect to erythromycin A, when the substrate (IV) is (8S)-8-fluoroerythronolide A, and to the antibiotic 3-O-oleandrosyl-5-O-desosaminyl-(8S)-8-fluoroerythronolide B (Scheme III: P-80204), having $R_{st}$ 0.82 with respect to erythromycin (IV) is (8S)-8-fluoroerithronolide B.

Scheme III

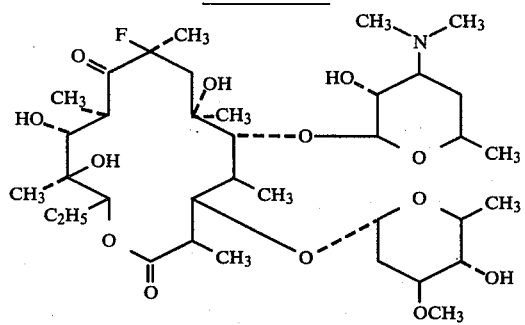

3-O-oleandrosyl-5-desosaminyl-(8S)-8-fluoroerythronolide A (P-80207)

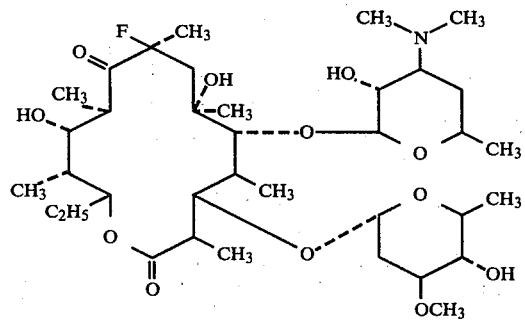

3-O-oleandrosyl-5-O-desosaminyl-(8S)-8-fluoroerythronolide B (P-80204).

The cultivation of the micro-organisms *Streptomyces erythreus* ATCC 31772 and *Streptomyces antibioticus* ATCC 31771 using the compounds (IV) as the substrate to produce the desired antibiotics can be carried out according to several fermentation methods.

After completion of the fermentation, various procedures can be used for the isolation and the purification of the antibiotics.

Among the methods suitable for the isolation and the purification the procedures of solvent extraction, both in batch form and in columns for the countercurrent liquid-liquid extraction, and the gel permeation chromatography are contemplated.

According to a preferred method, the antibiotics produced according to the present invention are recovered from the culture medium by separation of the mycelium and of any undissolved solids from the fermentation broth by conventional means such as by filtration or centrifugation. The antibiotics are then extracted from the filtered or centrifugated broth using either batchwise or counter current distribution extraction techniques.

The solvent extraction may be performed using a pH range of from 8 to 10 and employing as the solvent an inert organic solvent. Suitable solvents include alcohols, such as methanol, ethanol and the like, chlorinated hydrocarbons, such as chloroform, methylene chloride and the like, ethyl acetate, butyl acetate, amyl acetate, acetone, methylisobutylketone and acetonitrile, with methylisobutylketone being preferred. The final purification of the aforesaid antibiotics can be achieved by chromatography or permeable gels.

After filtration or centrifugation of the fermentation medium, thin layer chromatography or high pressure liquid phase chromatography can be employed to analise for the subject antibiotics.

In addition bioautography can also be used advantageously. The following examples illustrate the invention without being an undue limitation.

EXAMPLE 1

Preparation of the mutant *Streptomyces erythreus* ATCC 31772

A suspension of spores of *Streptomyces erythreus* producer of erythromycin subjected to mutagenic treatment with U.V. rays (emission maximum 250 nm) at a dose such as to kill about 99.6% of the spores (about 3000 erg/sq.cm).

The surviving spores were seeded on a plate of nutrient medium and the resulting colonies were analized with respect to their incapacity of producing erythromycin using the technique described by A. Kelner (1949) J. Bact. 57 73.

The mutants blocked in the synthesis of the erythromycin (about 2% of the surviving organisms) were then analized for their capacity of recognizing and converting the compound (IV) as a substrate into novel compounds having antibiotic activity.

EXAMPLE 2

Preparation of 8,9-anhydroerythronolide A-6,9-hemiacetal (II)

A solution of 4.185 g (0.01 moles) of erythronolide A (I), described by R. A. LeMahieu et al in J. Med. Chem. 17, 953 (1974), in 32 mls of glacial acetic acid was maintained on standing for two hours at room temperature. The acetic acid was then removed under vacuum at the temperature of 40° C. and the oily residue dissolved in 150 mls of chloroform. The chloroformic solution was washed with saturated solution of sodium bicarbonate and then with water upt to neutrality and lastly dried over $Na_2SO_4$.

After removal of the solvent under vacuum a raw product was obtained which was purified on a silica gel column, prepared in methylene chloride-methanol (1:1). The elution with methylene chloride-methanol (98:2) gave fractions containing only 8,9-anhydroerythronolide A-6,9-hemiacetal (II).

By evaporation to dryness of these combined fractions and subsequent crystallization from acetone/n-hexane there were obtained 2.750 g of the compound (II) having the following characteristics:

m.p. 188°-193° C.
$[\alpha]_D^{20}+20.5°$ (C=1 in methanol).
UV (MeOH) 210 nm ($\epsilon$6720).

IR (KBr) 3630, 3520, 3495, 3400, 1710, 1465, 1450, 1440, 1415, 1400, 1370, 1350, 1310, 1285, 1230, 1200, 1170, 1140, 1090, 1075, 1060, 1050, 1035, 1020, 1010, 1000, 970, 950, 940, 920, 915, 905, 890, 870, 825, 810, 800 cm$^{-1}$.

The analysis for $C_{21}H_{36}O_7$ gave the following values: calculated (%): C 62.97; H 9.06; found (%): C 63.12; H 9.10.

EXAMPLE 3

Preparation of (8S)-8-fluoroerythronolide A-6,9; 9,11-acetal (III) and (8S)-8-fluoroerythronolide A (IV) from 8,9-anhydroerythronolide A-6,9-hemiacetal (II)

A solution of fluoroxy-trifluoromethane in $CCl_3F$ at −80° C. was prepared: an excess of $CF_3OF$ (usually approximately twofold) was dissolved in $CCl_3F$ (precooled at −80° C. on dry ice) by slow addition of the gas through a purge tube (while the cylinder containing $CF_3OF$ was continuously weighed on a Sartorious electric balance).

Its concentration was determined by iodometric titration.

The $CF_3OF/CCl_3F$ solution at −80° C. or −85° C. was slowly added to a solution containing 4 g (0.010 moles) of 8,9-anhydroerythronolide A-6,9-hemiacetal in $CCl_3F/CH_2Cl_2$ (295 mls/370 mls) at about −80° C., magnetically stirred with calcium oxide (1.920 g) to remove hydrogen fluoride. Progress of the reaction was periodically monitored by high pressure liquid phase chromatography (HPLC), with respect to the disappearance of the characteristic peak of the compound (II).

After disappearance (or minimization) of the peak of the compound (II) the stirring was continued for 5 minutes and nitrogen gas was bubbled through the solution to remove excess $CF_3OF$ at −80° C. and the solution was allowed to warm to room temperature. The solution was washed with a saturated solution of $NaHCO_3$ (650 mls) and then washed neutral with water and finally dried over $Na_2SO_4$.

Removal of the solvent afforded a solid residue which was then purified by silica gel column chromatography (ratio 1:50), prepared in methylene chloride/methanol (1:1). The elution with increasing concentrations of methanol in methylene chloride gave fractions containing only (8S)-8-fluoroerythronolide A-6,9; 9,11-acetal (III) and fractions containing only (8S)-8-fluoro erythronolide A (IV). After evaporation to dryness of the fractions containing the compound (III) and their crystallization from acetone/n-hexane 3.435 g of product were obtained having the following characteristics:

m.p. 192°-3° C.; $[\alpha]_D^{20}+64.7°$ (C=1 in methanol).

U.V. (methanol); no adsorption corresponding to a ketone group.

IR (KBr): 3560, 3420, 1720, 1460, 1395, 1380, 1355, 1345, 1330, 1320, 1305, 1290, 1270, 1255, 1240, 1215, 1180 (broad), 1095, 1070, 1045, 1025, 1020, 990, 980, 970, 955, 940, 930, 920, 910, 905, 895, 855, 840, 830, 805 cm$^{-1}$.

The analysis for $C_{21}H_{35}FO_7$ gave the following values: calculated (%): C 60.27; H 8.43; F 4.54; found: (%): C 60.22; H 8.51; F 4.69.

After evaporation to dryness of the fractions containing the compound (IV) and crystallization from acetone/n-hexane 145 mg were obtained with the following characteristics:

m.p. 239°-240° C.; $[\alpha]_D^{20}-3.1°$ (C=1 in methanol).
UV (methanol): 287-8 nm ($\epsilon$25.3).

IR (KBr): 3610, 3550, 3480 (shoulder), 3380, (shoulder), 1735, 1700, 1460, 1405, 1390, 1380, 1350, 1325, 1290, 1270, 1175, 1105, 1090, 1050, 1035, 1020, 980, 960, 940, 920, 905, 895, 875, 860 cm$^{-1}$.

The analysis for $C_{21}H_{37}FO_8$ gave the following values: calculated (%): C 57.78; H 8.54; F 4.35 found (%): C 57.87; H 8.63; F 4.19

EXAMPLE 4

Preparation of (8S)-8fluoroerythronolide B-6,9; 9,11-hemiacetal (III) and (8S)-8-fluoroerythronolide B (IV) from 8,9-anhydroerythronolide B-6,9-hemiacetal (II).

By proceeding likewise the example 3, but starting from a solution containing 3.845 g (0.010 moles) of 8,9-anhydroerythronolide B-6,9-hemiacetal (II), (described in the U.S. Pat. No. 3,697,547), a raw product was obtained which, by crystallization from acetone/n-hexane, gave 3.450 g of (8S)-8-fluoroerythronolide B-6,9; 9,11-acetal (III), having the following characteristics:

m.p. 191°-2° C.; $[\alpha]_D^{20}=42.6°$ (C=1.0 in methanol).
UV (methanol); no adsorption corresponding to a ketone group.

IR (KBr): 3540, 3450, 1735, 1460, 1260, 1170, 1060, 1035, 980, 925, 875, 450 cm$^{-1}$.

The analysis for $C_{21}H_{35}FO_6$ gave the following values: calculated (%): C 62.67; H 8.76; F 4.72; found (%): C 62.63; H 8.82; F 4.81.

When the mother liquors were purified by silica gel column chromatography (ratio 1/50) with methylene chloride-methanol (98:2) as the eluant, 75 mg of a second product were obtained, (8S)-8-fluoroerythronolide B (IV) having the following characteristics:

m.p. 247°-8° C.; UV (methanol) 286 nm ($\epsilon$26).
$[\alpha]_D^{20}-30°$ (C=1 in methanol).
IR (KBr): 3540, 1727, 1703, 1460, 1330, 1270, 1175, 1130, 1075, 1050, 1015, 940, 920, 895, 860 cm$^{-1}$.

The analysis for $C_{21}H_{37}FO_7$ gave the following values: calculated (%): C 59.98; H 8.87; F 4.52; found: C 59.92; H 9.00; F 4.59.

EXAMPLE 5

Preparation of (8S)-8-fluoroerythronolide B (IV) from (8S)-8-fluoroerythronolide B-6,9; 9,11-acetal (III)

A mixture formed by 4.830 g (0.012 moles) of (8S)-8-fluoroerythronolide B-6,9; 9,11-acetal (III) and 3000 mls of an aqueous solution (pH)3) of acetic acid was refluxed at 110° C. for 15 minutes under stirring and then 220 mls of acetic acid were added. After one hour at 110° C. all the starting material was dissolved. The heating was continued for half a hour and the solution was then cooled as much rapidly as possible to room temperature, made neutral with NaHCO$_3$ and extracted with ethyl acetate.

The ethyl acetate solution after anhydrification over sodium sulphate was evaporated to dryness under vacuum.

When the raw product was purified by means of silica gel column chromatography (ratio 1:50) with methylene chloride-methanol (95:5) as the eluant, 1.8 g of a product were obtained having chemical and physical properties equal to those of the compound (IV) isolated in the example 4.

EXAMPLE 6

A solution of 5.465 g (0.010 moles) of 3-O-mycarosyl-erythronolide B (I), described by J. R. Martin in biochemistry, 5, 2852 (1966), in 32 mls of glacial acetic acid was maintained on standing for 2 hours at room temperature.

The acetic acid was then removed under vacuum at the temperature of 40° C. and the oily residue was dissolved in 150 mls of chloroform.

The chloroform solution was washed with a saturated solution of sodium bicarbonate and then with water to neutrality and lastly dried on Na$_2$SO$_4$. After removal of the solvent under vacuum a raw product was obtained which was purified on silica gel column (ratio 1:100), prepared in chloroform.

The elution with increasing concentrations of methanol in chloroform gave fractions containing only 3-O-mycarosyl-8,9-anhydroerythronolide B-6,9-hemiacetal (II).

By evaporation to dryness of these combined fractions and subsequente crystallization from acetone/n-hexane 1.160 g of the compound (II) were obtained having the following characteristics:

m.p. 85°-88° C.; $[\alpha]_D^{20} - 5°$ (C=1 in methanol).

UV (MeOH): 210 nm ($\epsilon$6850).

IR (KBr): 3500, 1730, 1465, 1415, 1380, 1340, 1185, 1120, 1085, 1055, 1005, 985, 945, 895, 810 cm$^{-1}$.

The analysis for C$_{28}$H$_{48}$O$_9$ gave the following values: calculated (%): C 63.61; H 9,15; found (%) C 63.52; H 9.09.

EXAMPLE 7

Preparation of 3-O-mycarosyl-(8S)-8-fluoroerythronolide B-6,9; 9,11-acetal (III) and 3-O-mycarosyl-(8S)-fluoroerythronolide B (IV) from 3-O-mycraosyl-8,9-anhydroerythronolide B-6,9-hemiacetal (II).

A solution of fluoroxy-trifluoromethane in CCl$_3$F at $-80°$ C. was prepared: an excess of CF$_3$OF (usually about two fold) was dissolved in CCl$_3$F (precooled at $-80°$ C. or at $-85°$ C.) was slowly added to a solution containing 5.285 g (0.010 moles) of 3-O-mycarosyl-8,9-anhydroerythronolide B-6,9-hemiacetal (II) in CCl$_3$F/CH$_2$Cl$_2$ (295 mls/370 mls) at about $-80°$ C., magnetically stirred with calcium oxide (1.920 g) to remove the hydrogen fluoride.

The progress of the reaction was periodically mentioned by high pressure liquid chromatography (HPLC), with respect to the disappearance of the peak characteristic of the compound (II).

After disappearance (or minimization) of the peak related to the compound (II), the stirring was continued for further 5 minutes and nitrogen gas was bubbled through the solution to remove the excess of CF$_3$OF at $-80°$ C. and the solution was allowed to warm to room temperature. The solution was washed with a saturated solution of NaHCO$_3$ (650 mls) and then washed to neutrality with water and lastly dried over Na$_2$SO$_4$. From the solvent removal a solid residue was obtained which was then purified by silica gel column chromatography (ratio 1:100), preparated in chloroform.

The elution with increasing concentrations of methanol in chloroform gave fractions containing only 3-O-mycarosyl-(8S)-fluoroerythronolide B-6,9; 9,11-acetal (III) and fractions containing only 3-O-mycarosyl-(8S)-8-fluoroerythronolide B (IV).

After evaporation to dryness of the fractions containing the compound (III) and their crystallization from acetone 1.100 g were obtained having the following characteristics:

m.p. 175°-7° C.

$[\alpha]_D^{20} - 9.8°$ (C=1 in methanol).

UV (methanol); no adsorption corresponding to a ketone group.

IR (KBr): 3540, 3490, 1720, 1460, 1395, 1380, 1365, 1355, 1330, 1320, 1290, 1275, 1265, 1245, 1025, 1185, 1165, 1145, 1120, 1100, 1080, 1060, 1045, 1015, 1005, 990, 960, 940, 925, 915, 900, 880, 865, 840, 815 cm$^{-1}$.

The analysis for C$_{28}$H$_{47}$FO$_9$ gave the following values: calculated (%): C 61.52; H 8.67; F 3.47; found (%): C 61.46; H 8.51; F 3.48.

After evaporation to dryness of the fractions containing the compound (IV) and crystallization from acetone/n-hexane, 290 mg were obtained of a product having the following characteristics:

m.p. 214°-5° C.;

$[\alpha]_D^{20} - 73.2°$ (C=1 methanol).

UV methanol 287 nm ($\epsilon$25.3).

IR (KBr): 3570, 3550, 3530, 3460 (shoulder), 1745, 1735, 1465, 1380, 1365, 1340, 1300, 1275, 1250, 1180, 1115, 1080, 1055, 1010, 1000 (shoulder), 985, 945, 935, 920, 895, 855, 840, 810 cm$^{-1}$.

The analysis for C$_{28}$H$_{49}$FO$_{10}$ gave the following values: calculated (%): C 59.55; H 8.75; F 3.37; found (%): C 59.68; H 8.60; F 3.48.

EXAMPLE 8

Preparation of 3-O-mycarosil-(8S)-8-fluoroerythronolide B (IV) from 3-O-mycarosyl-(8S)-8-fluoroerythronolide B-6,9; 9,11-acetal (III)

A mixture formed by 6.560 g (0.012 moles) of 3-O-mycarosil-(8S)-8-fluoroerythronolide B-6,9; 9,11-acetal (III) and 3000 mls of a water solution (pH 3) of acetic acid was maintained at room temperature under stirring until completely dissolved and then 220 mls of acetic acid were added.

The solution was left under stirring at room temperature until the starting compound (III) completely disappeared, (the control being effected by high pressure liquid chromatography), made neutral with NaHCO$_3$, and extracted with ethyl acetate. The ethyl acetate solution, after anhydrification over sodium sulphate, was evaporated to dryness under vacuum.

When the raw product was purified by means of silica gel column chromatography (ratio 1:50) with methylene chloride-methanol (95:5) as the eluant, a product was obtained having chemical and physical characteristics equal to those of the compound (IV) isolated in the example 7.

EXAMPLE 9

Preparation of (8S)-8-fluoroerythronolide A (IV) from (8S)-8-fluoroerythronolide A-6,9; 9,11-acetal (III)

A mixture formed by 5.020 g (0.012 moles) of (8S)-8-fluoroerythronolide A-6,9; 9,11-acetal (III) and 3000 mls of a water solution (pH 3) of acetic acid was refluxed at 110° C. for 15 minutes under stirring and then 220 mls of acetic were added. After one hour at 110° C. all the starting material was dissolved.

The heating was continued for half a hour and the solution was thereafter cooled as much rapidly as possible to room temperature, made neutral with NaHCO$_3$ and extracted with acetic acid.

The solution of ethyl acetate, after anhydrification over sodium sulphate, was evaporated to dryness under vacuum.

The raw solid was then purified by means of silica gel column chromatography (ratio 1:10), prepared in methylene chloride.

The elution with increasing concentrations of methanol in methylene chloride gave fractions still containing starting compound (8S)-8-fluoroerythronolide A-6,9; 9,11-acetal (III) and fractions containing only (8S)-8-fluoroerythronolide A (IV).

By repeating the reaction on the recovered starting compound and carrying out subsequently the chromatographic purification other fractions containing (8S)-8-fluoroerythronolide A were obtained.

By evaporation to dryness of all the combined fractions and then recrystallization of the resulting solid 0.725 g of (8S)-8-fluoroerythronolide A (IV) were obtained having the same characteristics reported in the example 3.

EXAMPLE 10

Preparation of the antibiotics (8S)-8-fluoroerythromycin C (P-80206) and (8S)-8-fluoroerythromycin A (P-80205).

A seeded culture of Streptomyces erythreus ATCC 31772, a mutant blocked in the synthesis of erythromycin, was prepared in a medium comprising (in grams per liter); sucrose 30.0; cane molasses 8.0 soy bean oil 9.0; (NH$_4$)$_2$SO$_4$S.O; CaCO$_3$7.0.

The culture was incubated at 33° C. for 48 hours on a rotary shaker. The seed was added at a level of 5% (V/V) into 250 ml Erlenmeyer flasks containing 30 mls of a fermentation medium having the following composition (in grams per liter): corn dextrins 30.0; raw corn starch 40.0; soy bean meal 30.0; soy bean oil 20.0; (NH$_4$)$_2$SO$_4$2.0; and CaCO$_3$6.0.

The fermentation flasks were incubated at 33° C. on a rotary shaker (220 rpm, 4 cm stroke) for 24 hours.

Fifteen milligrams of finely divided (8S)-8-fluoroerythronolide B (III) sterilized under UV light for 15 minutes were added to each flask, and the incubation with shaking was continued for 96 hours.

Treatment of the samples by thin layer chromatography and by high pressure liquid phase chromatography At the end of the fermentation time a sample of the fermentation broth assaying about 900–1000 mcg/ml (titre expressed as erythrhomycin A) was centrifuged and the surnatant liquid was clarified by adding equal volumes of a 10% (W/V) of aqueous solution of ZnSO$_4$ and a 4% (W/V) of aqueous solution of sodium hydroxide. After centrifugation the clear surnatant liquid was extracted by vortexing with one third of its volume of ethyl acetate.

TLC CONTROL

A sample of the organic phase was spotted on a silica gel G plate and developed in CH$_2$Cl$_2$-MetOH-H$_2$O-conc. NH$_4$OH (90:9.5:0.5:1) for 2 hours; the spots were located with the spray reagent comprising methanol-anisaldehyde-conc.sulfuric acid: acetic acid, (85:0.5:5:10) and the active compounds were revealed by means of bioautography on plates seeded with Micrococcus luteus (Sarcina lutea) ATCC 9341.

The results of the TLC showed the disappearance of the added (8S)-8-fluoroerythronolide A (IV) and the appearance of the two active compounds the R$_{st}$ values of which with respect to erythromycin A are respectively 0.89 and 1.12 (0.087 and 1.040 with respect to the erythromycin B). Furthermore they show different chromatic reactions after application of a spray reagent and heating: dark brown (hot) for the slowest compound (antibiotic P-80205) and dark violet colour (after cooling) for the other compound (antibiotic P-8206).

HPLC CONTROL

A sample of the organic phase is evaporated to dryness, taken with acetonitrile and injected in the column (RP8 10 μm 25 cm; mobile phase phosphate buffer 0.01 M pH 7/acetonitrile 36:64; flow 2 mls/min.; column temperature 40° C.). Two peaks are detected having retention time with respect to erythromycin A of 0.68 (P-80205) and of 0.87 (P-80206).

EXAMPLE 11

Purification of the antibiotics (8S)-8-fluoroerythromycin C (P-80205) and (8S)-8-fluoroerythromycin A (P-80206).

According to the process described in the preceding example, several fermentations of a total volume of 2100 mls to which 1.00 g of (8S)-8-fluoroerythronolide A had been added, were filtered under vacuum after addition under stirring of Hyflo Supercell (4% W/V).

The solid was washed with water and the combined filtrates were adjusted to pH 5.5 with acetic acid. The acidic aqueous solution was extracted three times with an equal volume of ethyl acetate. The acquous aqueous was neutralized with 2 N NH$_4$OH and evaporated under reduced pressure to a volume of 1000 mls, adjusted to pH 8.8 with 2 N NH$_4$OH and extracted with an equal volume of methylisobutylketone. The latter organic extracts were combined and washed two times with half a volume of 0.1 M KH$_2$PO$_4$ and then one time more with water.

After drying (Na$_2$SO$_4$) and removal of the solvent under vacuum, the residue was purified by silica gel column chromatography according to the method disclosed by N. L. Oleinick in J. Biol. Chem., Vol. 244, n. 3, pag. 727 (1969).

The fractions 90 to 174 containing only the antibiotic P-80206 were combined and evaporated to dryness at 40° C. The solid residue by crystallization from absolute ethanol gave 230 mg of (8S)-8-fluoro erythromcyin A (P-80206) having the following characteristics:

m.p.: 183°–4° C.; $[\alpha]_D^{20}-55°$ (C=1 in methanol).

UV (methanol): 283 nm ($\epsilon$17.9).

IR (KBr): 3520, 3480 (shoulder), 1735, 1720, 1460, 1425, 1400, 1370, 1345, 1330, 1305, 1280, 1190, 1170, 1120, 1090, 1075, 1055, 1030, 1015, 1005, 980, 960 (shoulder), 935, 890, 870, 855, 835, 800 cm$^{-1}$ (this spectrum is shown in FIG. 1).

The analysis for C$_{37}$H$_{66}$FNO$_{13}$ gave the following values: calculated (%): C 59.10; H 8.85; F 2.52; N 1.86. found (%): C 59.09; H 8.89; F 2.59; N 1.88.

The fractions 280 to 400 containing only the antibiotic P-80205 were combined and evaporated to dryness at 40° C. under vacuum. The solid residue by crystallization from absolute ethanol gave 145 mg of (8S)-8-fluoroerythromycin C (P-80205) having the following characteristics:

m.p. 217°–8° C.

$[\alpha]_D^{20} -42.35°$ (C=1 in methanol).

UV (methanol): 284 nm ($\epsilon$23.2).

IR (KBr): 3550, 3500, 3440 (shoulder), 3300 (broad), 1730, 1455, 1425, 1410, 1380, 1360, 1340, 1330, 1305, 1280, 1270, 1245, 1200 (shoulder), 1170 (broad), 1115, 1090, 1075, 1060, 1030, 1010, 1000, 980 (shoulder), 965, 955, 945, 935, 920, 905, 895, 870, 840, 830, 810 cm$^{-1}$. (the related spectrum is shown in FIG. 2).

The analysis for $C_{36}H_{64}FNO_{13}$ gave the following values: calculated (%): C, 58.60; H 8.74; F 2.57; N 1.90; found (%): C 58.47; H 8.87; F 2.60; N 1.82.

EXAMPLE 12

Preparation of the antibiotic 3-O-oleandrosyl-5-O-desosaminyl-(8S)-8-fluoroerythronolide A (P-80207).

A preseed culture of S.antibioticus ATCC 31771, a mutant blocked in the biosynthesis of oleandomycin, was prepared in a medium comprising (in grams per liter of deionized water) soy bean meal 30.0; cerelose 15.0; yeast autolysate 1.0; soy bean oil 30.0; $MgSO_4.7H_2O$ 1.0; and $CaCO_3$ 10.0, the pH of the medium being adjusted to 7.2 before the sterilization.

After 24 hours at 28° C. on a rotary shaker, this culture was utilized for the seeding of the same medium at a concentration of 2% (V/V) and was further incubated under the same conditions for 16 hours. This seed was added at the concentration of 3% (V/V) in 250 ml Erlenmeyer flasks containing 30 mls of a fermentation medium having the following composition (grams per liter): cerelose 40.0; soy bean meal 20.0; maize meal 3.0; dried baker yeast 2.0; $CaCO_3$ 20.0.

For the fermentation the flasks were incubated at 28° C. on a rotary shaker (240 rpm, 4 cm stroke) for 32 hours; 15 mg of finely divided (8S)-8-fluoroerythronolide A (IV) were added to each flask and the incubation with stirring was continued for 64 hours.

At the end of this period the titre of the culture, expressed as erythromycin A, was 100°–120° C. mcg/ml. The treatment of the fermentation broth for the TLC analysis was carried out with the system and under the conditions indicated in the example 10.

TLC CONTROL

According to the technique described in the example 10 a novel active compound (antibiotic P-80207) is revealed, indicating the disappearance of the added substrate. The Rf thereof with respect to erythromycin A is 0.80 and with respect to elandomycin is 0.87.

HPLC CONTROL

According to the technique described in the example 10, the novel active compound (antibiotic P-80207) has a retention time with respect to erythromycin A of 0.69 and with respect to oleandomycin of 0.95.

EXAMPLE 13

Purification of the antibiotic 3-O-oleandrosyl-5-O-desosaminyl-(8S)-8-fluoroerythronolide A (P-80207).

The total culture broth, deriving from 50 fermentations carried out in Erlenmeyer flasks, under stirring and effected according to the preceding example 12, was treated with an equal volume of methanol. After the addition of Hyflo Supercell over 30 minutes under stirring, the mixture was filtered. The solid was washed with water/methanol (1:1) and the combined filtrates were evaporated under reduced pressure to half the starting volume.

The pH of the solution was adjusted to 8.2 by addition of KOH and the solution was extracted three times with amounts corresponding to one third of the volume of methylisobutylketone. The extracts with organic solvent, combined, were washed with 0.1 M $Na_2HPO_4$ and then with water.

The organic solution, after anhydrification over $Na_2SO_4$, was evaporated to dryness under vacuum. The residue was purified by chromatography on silica gel column according to the method described in example 11.

The fractions 45 to 80 containing only the antibiotic P-80207 were combined and brought to dryness under vacuum at 40° C. The solid residue was crystallized from absolute ethanol to obtain 130 mg of 3-O-oleandrosyl-5-O-desosaminyl-58S)-8-fluoroerythronolide A (P-80207) having the following characteristics:

m.p.: 155°–7° C.

$[\alpha]_D^{20} -40.2°$ (C=1 in methanol).

UV (methanol): 283 nm ($\epsilon$ 20.3).

IR (KBr): 3480 (broad), 1730, 1510, 1380, 1340 (broad), 1305, 1275, 1195, 1165, 1105, 1095, 1075, 1050, 1030, 1010, 1000, 980, 960 (shoulder), 935, 915, 895, 875, 830 cm$^{-1}$. (this spectrum is shown in FIG. 3).

The analysis for $C_{36}H_{64}FNO_{13}$ gave the following values: calculated (%): C 58.60; H 8.74; F 2.57; N 1.90; found (%): C 58.52; H 8.75. F 2.63; N 1.95.

EXAMPLE 14

Preparation of the antibiotics (8S)-8-fluoroerythromycin D (P-80202) and (8S)-8-fluoroerythromycin B (P-80203).

A seeded culture of Streptomyces erythreus ATCC 31772, a mutant blocked in the biosynthesis of erythromycin, was prepared in a medium comprising (in grams per liter) sucrose 30.0; cane molasses 8.0; soy bean oil 9.0; $(NH_4)_2SO_2$ 2.0; $CaCO_3$ 7.0.

The culture was incubated at 33° C. for 48 hours on a rotary shaker.

The seed was added at a level of 5% (V/V) to 250 ml Erlenmeyer flasks containing 30 mls of a fermentation medium having the following composition in grams per liter: corn dextrins 30.0; raw corn starch 40.0; soy bean meal 30.0; soy bean oil 20.0; $(NH_4)_2SO_4$ 2.0; $CaCO_3$ 6.0.

The fermentation flasks were incubated at 33° C. for 24 hours on a rotary shaker (220 rpm, 4 cm stroke).

15 mg of (8S)-8-fluoroerythronolide B (IV) in a finely divided form and sterilized under ultraviolet light for 15 minutes were added to each flask, and the incubation with shaking was continued for 96 hours.

Treatment of the sample by thin layer chromatography (TLC) and high pressure liquid phase chromatography (HPLC)

At the end of the fermentation period a sample of the fermentation broth having an activity of about 900–1000 mcg/ml (titre expressed as eryhtromycin A) was centrifugated and the surnatant liquid was clarified by adding equal volumes of 10% (W/V) aqueous solution of $ZnSO_4$ and of a 4% (W/V) aqueous solution of sodium hydroxide.

After centrifugation the surnatant clear liquid was extracted by vortexing with one third of its volume of ethyl acetate.

TLC CONTROL

A sample of the organic phase was deposited onto a silica gel G plate and developed in CH$_2$Cl$_2$-MetOH-H$_2$O-conc. NH$_4$OH (90:9.5:0.5:1) for 2 hours; the spots were located by means of a spray reactant comprising methanol-anisaldehyde-conc. sulfuric acid-acetic acid (85:0.5:5:10) and the active compounds were detected by bioautography on plates seeded with Microccus luteus (Sarcina lutea) ATCC 9341. The results of the TLC showed the disappearance of the added (8S)-8-fluoroerythronolide B (IV) and the appearance of two active compounds, the $R_{st}$ values of which with respect to erythromycin A are respectively 0.9 and 1.13 (0.85 and 1.06 with respect to erythromycin B). Furthermore they show different chromatic reactions after application of a spray reactant and heating; dark brown colour (under hot conditions) for the slowest compound (antibiotic P-80202) and dark violet colour (after cooling) for the other compound (antibiotic P-80203).

HPLC CONTROL

A sample of the organic phase is evaporated to dryness, taken with acetonitrile and injected in column (RP8 10 μm 25 cm; mobile phase phosphate buffer 0.01 M pH 7/acetonitrile 36.64; flow 2 mls/min.; column temperature 40° C.). Two peaks are revealed with a retention time with respect to erythromycin A of 0.79 (P-80202) and 1.06 (P-80203).

EXAMPLE 15

Purification of the antibiotics (8S)-8-fluoroerythromycin D (P-80202) and (8S)-8-fluoroerytrhomycin B (P-80203)

According to the procedure described in the preceding example 14, several fermentations for a total volume of 2100 mls, which had been supplemented with 1.0 g of (8S)-8-fluoroerythronolide B were filtered under vacuum after addition under stirring of Hyflo Supercell (4% weight/volume). The solid was washed with water and the combined filtrates were adjusted to pH 5.5. with acetic acid. The acidic aqueous solution was extracted three times with an equal volume of ethyl acetate. The aqueous phase was neutralized with 2 N NH$_4$OH, evaporated at reduced pressure to a volume of 1000 mls, adjusted to a pH of 8.8 with 2 N NH$_4$OH and extracted with an equal volume of methylisobutylketone.

The latter organic extracts were combined and washed two times with half a volume of 0.1 M KH$_2$PO$_4$ and then a further time with water. After drying (Na$_2$SO$_4$) and removal of the solvent under vacuum, the residue was purified by silica gel column chromatography according to the procedure described by N. L. Oleinick in J. Biol. Chem. Vol. 244, n. 3 pag. 727 (1969).

The fractions 18 to 32 containing only the antibiotic P-80203 were combined and brought to dryness under vacuum at 40° C. The solid residue by crystallization from absolute ethanol gave 150 mg (of (8S)-8-fluoroerythromycin B (P-80203) having the following characteristics:

m.p.: 164°-6° C.
$[\alpha]_D^{20}$ −63° (C=1 in methanol).
UV (methanol): 285 nm (ε 29.5).
IR (KBr): 3480 (broad), 1735, 1465, 1435, 1385, 1375, 1330, 1305, 1280, 1170, 1115, 1090, 1075, 1055, 1035, 1020, 1000, 975, 940, 890, 835, 805 cm$^{-1}$ (FIG. 4).

The analysis for C$_{37}$H$_{66}$FNO$_{12}$ gave the following values: calculated (%): C 60.39; H 9.04; F 2.58; N 1.90; found (%): C 60.31; H 9.09; F 2.60; N 1.88.

The fractions 55 to 105 containing only the antibiotic P-80202 were combined and brought to dryness under vacuum at 40° C. The solid residue by cristallization from absolute ethanol gave 150 mg of (8S)-8-fluoroerythromycin D (P-80202) having the following characteristics:

m.p. 213°-15° C.
$[\alpha]_D^{20}$ −60° (C=1 in methanol).
UV (methanol): 285 nm (ε 30.8).
IR (KBr): 3600, 3520, 3300 (broad), 1730, 1460, 1420, 1385, 1370, 1355, 1345, 1330, 1310, 1275, 1190, 1160, 1120, 1100, 1060, 1040, 1030, 1010, 1000, 995, 975, 960, 935, 920, 910, 890, 875, 840, 825, 810 cm$^{-1}$ (FIG. 5).

The analysis for C$_{36}$H$_{64}$FNO$_{12}$ gave the following results: calculated (%): C 59.89; H 8.94; F 2.63; N 1.94; found (%): C 59.87; H 8.85; F 2.63; N 1.88.

EXAMPLE 16

Preparation of the antibiotic 3-O-oleandrosyl-5-O-desosaminyl-(8S)-8-fluoroerythronolide B (P-80204).

A preseeded culture of S.antibioticus ATCC 31771, a mutant blocked in the biosynthesis of oleandomycin, was prepared in a medium comprising (in grams per liter of deionized water) soy bean meal 30.0; cerelose 15.0; yeast autolysate 1.0; soy bean oil 30.0; MgSO$_4$.7-H$_2$O 1.0; CaCO$_3$ 10.0; the pH of the medium being adjusted to 7.2 before the sterilization.

After 24 hours at 28° C. on rotary shaker, this culture was used for the seeding of the same medium at a concentration of 2% (V/V) and was further incubated under the same conditions for 16 hours.

This seed was added at the concentration of 3% (V/V) to 250 ml Erlenmeyer flasks containing 30 mls of a fermentation medium having the following composition (grams per liter): cerelose 40.0; soy bean meal 20.0; maize meal 3.0; dried baker yeast 2.0; CaCO$_3$ 20.0.

The flasks for the fermentation were incubated at 28° C. on a rotary shaker (240 rpm, 4 cm stroke) for 32 hours; 15 mg of finely divided (8S)-8-fluoroerythronolide B were added to each flask and the incubation under stirring was continued for 64 hours.

At the end of this period the titre of the culture expressed as erythromycin A was 100–120 mcg/ml. The treatment of the fermentation broth for the TLC analysis was carried out with the system and under the conditions indicated in the example 14.

TLC CONTROL

According to the technique indicated in the example 14 a novel active compound is detected (antibiotic P-80204), which follows the disappearance of the added substrate. The $R_{st}$ thereof with respect to the erythromycin B is 0.82 and with respect to oleandomycin is 0.90.

HPLC CONTROL

According to the technique indicated in the example 14 the novel active compound (P-80204) has a retention time with respect to erythromycin B of 0.62 and with respect to the oleandomycin of 1.06.

EXAMPLE 17

Purification of the antibiotic 3-O-oleandrosyl-5-O-desosaminyl-(8S)-8-fluoroerythronolide B (P-80204).

The total culture broth deriving from fifteen fermentations, carried out in Erlenmeyer flasks, stirred and under the conditions described in the preceding example 16, was treated with an equal volume of methanol. After the addition of the Hyflo Supercell in 30 mls under stirring the mixture was filtered. The solid was washed with water-methanol (1:1) and the combined filtrates were evaporated under reduced pressure to half of the starting volume.

The pH of the solution was adjusted to 8.2 by adding KOH and the solution was extracted three times with an amount of one third of the volume of methylisobutylketone.

The combined extracts with organic solvent were washed with 0.1 M $NaH_2PO_4$ and then with water. The organic solution after anhydrification over $Na_2SO_4$ was evaporated to dryness under vacuum. The residue was purified by means of silica gel column chromatography according to the technique indicated in the example 15.

The fractions 17 to 42 containing only the antibiotic P-80204 were combined and brought to dryness under vacuum at 40° C. The solid residue was further purified in a Sephadex LH-20 column (2×98 cm) preparated in hexane-chloroform (1:1) and eluted with the same solvent.

The fractions containing only the novel antibiotic P-80204 were combined and concentrated to dryness under vacuum at 40° C. to give, after crystallization from acetone-hexane, 170 mg of 3-O-oleandrosyl-5-O-desosaminyl-(8S)-8-fluoroerythronolide B (P-80204) having the following characteristics:

m.p.: 195°-6° C.

$[\alpha]_D^{20} - 48°$ (C=1 in methanol).

UV (methanol): 285 nm ($\epsilon$ 29).

Figure 6:
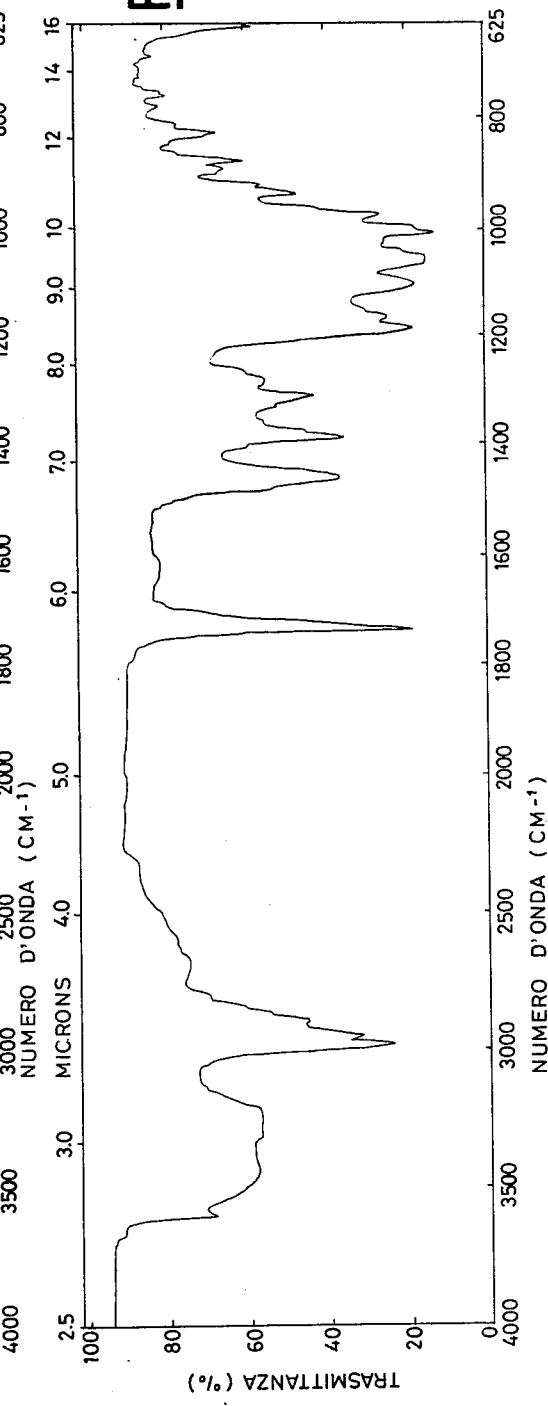

IR (KBr): 3600, 3440 (broad), 3250, 1730, 1455, 1400, 1380, 1365, 1350, 1325, 1305, 1270, 1255, 1180, 1160, 1145, 1100, 1060, 1040, 1010, 995, 975, 960, 935, 915, 890, 875, 855, 845, 830, 820 cm$^{-1}$ (FIG. 6).

The analysis for $C_{36}H_{64}FNO_{12}$ gave the following values: calculated (%): C 59.89; H 8.94; F 2.63; N 1.94; found (%): C 59.94; H 9.06; F 2.69; N 1.83.

EXAMPLE 18

Preparation of the antibiotic (8S)-8-fluoroerythromycin D (P-80202° and (8S)-8-fluoroerythromycin B (P-80203)

A seeded culture of *Streptomyces erythreus* ATCC 31772, a mutant blocked in the biosynthesis of erythromycin, was prepared in a medium comprising (in grams per liter) sucrose 30.0; cane molasses 8.0; soy bean oil 9.0; $(NH_4)_2SO_4$ 2.0; $CaCO_3$ 7.0.

The culture was incubated for 48 hours at 33° C. on rotary shaker.

The seed was added at a level of 5% (V/V) to 250 ml Erlenmeyer flasks containing 30 mls of a fermentation medium having the following composition in grams per liter: raw corn starch 40.0; corn dextrins 30.0; soy bean meal 30.0; soy bean oil 20.0; $(NH_4)_2SO_4$ 2.0; $CaCO_3$ 6.0.

The fermentation flasks were incubated at 33° C. on rotary shaker (220 rpm, 4 cm stroke) for 24 hours.

15 mg of finely divided 3-O-mycarosyl-(8S)-8-fluoro-erythronolide B (IV) sterilized under ulraviolet light for 15 minutes were added to each flask and the incubation with shaking was continued for 96 hours.

Treatment of the samples by thin layer chromatography (TLC) and by high pressure liquid phase chromatography (HPLC)

At the end of the fermentation period a sample of the fermentation broth having an activity of about 900-1000 mcg/ml (titre expressed as erythromcin A) was centrifugated and the surnatant liquid was clarified by adding equal volumes of a 10% (W/V) aqueous solution of $ZnSO_4$ and of a 4% (W/V) aqueous solution of sodium hydroxide. After centrifugation the clear surnatant liquid was extracted by vortexing with one third of its volume of ethyl acetate.

TLC CONTROL

A sample of the organic phase was deposited on a silica gel G plate and developed in $CH_2Cl_2$-MetOH-$H_2O$-conc. $NH_4OH$ (90:9.5:0.5:1) for 2 hours; the spots were located wih a spray reagent comprising methanol-anisaldehyde-conc. sulfuric acid-acetic acid (85:0.5:5:10) and the active compounds were revealed by means of bioautography on plates seeded with *Micrococcus luteus* (*Sarcina lutea*) ATCC 9341.

The results of the TLC showed the disappearance of the added 3-O-mycarosyl-(8S)-8-fluoroerythronolide B (IV) and the appearance of the two active compounds having $R_{st}$ with respect to erythromycin A of 0.9 and 1.13 respectively (0.85 and 1.06 with respect to erythromycin B).

Furthermore they show different chromatic reactions after application of a spray reagent and heating; dark brown colour (hot) for the slowest compound (antibiotic P-80202) and dark violet colour (after cooling) for the second compound (antibiotic P-80203).

HPLC CONTROL

A sample of the organic phase wase evaporated to dryness, taken with acetonitrile and injected in column (RP8 10 $\mu$m 25 cm; mobile phase phosphate buffer 0.01 M pH 7/acetonitrile 36.64; flow 2 mis/min.; column temperature 40° C.). Two peaks are revealed having a retention time with respect to erythromycin A of 0.79 (P-80202) and 1.06 (P-80203).

EXAMPLE 19

Purification of the antibiotics (8S)-8-fluoroerythromycin D (P-80202) and (8S)-8-fluoroerythromycin B (P-80203).

According to the precedure described in the preceding example 18, several fermentations for a total volume of 2100 mls, which had been added with 1.0 g 3-O-mycarosyl-(8S)-8-fluoroerythronolide B were filtered under vacuum after addition under stirring of Hyflo Supercell (4% weight/volume).

The solid was washed with water and the combined filtrates were adjusted to pH 5.5 with acetic acid.

The acidic water solution was extracted three times with an equal volume of ethyl acetate. The aqueous phase was neutralized with 2 N $NH_4OH$ and evaporated under reduced pressure to a volume of 1000 mls, adjusted to pH 8.8 with 2 N $NH_4OH$ and extracted with an equal volume of methylisobutylketone.

The latter organic extracts were combined and washed two times with half a volume of 0.1 M $KH_2PO_4$ and then a further time with water. After drying ($Na_2SO_4$) and removal of the solvent under vacuum, the residue was purified by means of silica gel column chromatography according to the technique described by N.

L. Oleinick, in J. Biol. Chem., Vol. 244, n. 3, page 727 (1969).

The fractions 23 to 38 containing only the antibiotic P-80203 were combined and brought to dryness under vacuum at 40° C. The solid residue, by crystallization from absolute ethanol, gave 165 mg of (8S)-8-fluoroerythromycin B (P-80203) having the following characteristics:

m.p.: 164°–6° C.
$[\alpha]_D^{20} -63°$ (C=1 in methanol).
UV (methanol): 285 mm ($\epsilon$ 29.5).
IR (KBr): 3480 (broad), 1735, 1465, 1435, 1385, 1375, 1330, 1305, 1280, 1170, 1115, 1090, 1075, 1055, 1035, 1020, 1000, 975, 940, 890, 835, 805 cm$^{-1}$.

The analysis for $C_{37}H_{66}FNO_{12}$ gave the following values: calculated (%): C 60.39; H 9.04; F 2.58; N 1.90; found (%): C 60.31; H 9.09; F 2.60; N 1.88.

The fractions 65 to 120 containing only the antibiotic P-80202 were combined and brought to dryness under vacuum at 40° C. The solid residue by crystallization from absolute ethanol gave 125 mg of (8S)-8-fluoroerythromycin D (P-80202) having the following characteristics:

m.p. 213°–5° C.
$[\alpha]_D^{20} -60°$ (C=1 in methanol).
UV (methanol): 285 nm ($\epsilon$ 30.8).
IR (KBr); 3600, 3520, 3300 (broad), 1730, 1460, 1420, 1385, 1370, 1355, 1345, 1330, 1310, 1275, 1190, 1160, 1120, 1100, 1060, 1040, 1030, 1010, 1000, 995, 975, 960, 935, 920, 910, 890, 875, 840, 825, 810 cm$^{-1}$.

The analysis for $C_{36}H_{64}FNO_{12}$ gave the following values; calculated (%): C 59.85; H 8.94; F 2.63; N 1.94; found (%): C 59.87; H 8.85. F 2.63; N 1.88.

EXAMPLE 20

Preparation of (8S)-8-fluoroerythromycin A acetate

To a solution of 7.520 g (0.010 moles) of (8S)-8-fluoroerythromycin A in 30 mls of anhydrous acetone containing 3.760 g of sodium bicarbonate 1.23 mls (0.013 moles) of acetic anhydride were added.

The mixture was maintained under stirring at 25° C. for 2 hours and then poured in water-ice. After 2 hours it was extracted three times with chloroform, rapidly washed with a saturated solution of sodium bicarbonate and then with water.

The chloroformic solution was dried over anhydrous $Na_2SO_4$ and evaporated under vacuum to dryness to give 7.545 g of solid residue.

By crystallization of the solid from ethyl ether-hexane-n 6.325 g of (8S)-8-fluoroerythromycin A acetate were obtained having the following characteristics:

m.p. 130°–5° C.
$[\alpha]_D^{20} -52°$ (C=1 in acetone).
IR (KBr): 3480, 1740, 1455, 1370, 1340, 1280, 1235, 1160, 1110, 1085, 1050, 1030, 1010, 995, 975, 955, 930, 890, 870, 830, 800 cm$^{-1}$.

The analysis for $C_{39}H_{68}FNO_{14}$ gave the following values: calculated (%): C 59.00; H 8.63; F 2.39; N 1.76; found (%): C 59.32; H 8.75; F 2.32; N 1.79.

EXAMPLE 21

Preparation of (8S)-8-fluoroerythromycin A propionate

Using the general method of the example 20 (8S)-8-fluoroerythromycin A was converted into (8S)-8-fluoroerythromycin propionate by esterification with propionic anhydride. The final product had the following characteristics:

m.p. 115°–20° C. (ethyl ether/n-hexane).
$[\alpha]_D^{20} -56.5°$ (C=1 in acetone).
IR (KBr): 3480, 1735, 1455, 1375, 1340, 1180, (shoulder), 1160, 1080, 1050, 1030, 995, 975, 955, 930, 890, 800 cm$^{-1}$.

The analysis for $C_{40}H_{70}FNO_{14}$ gave the following values: calculated (%): C59.46; H 8.83; F 2.31; N 1.70; found (%): C 60.13; H 8.71; F 2.27; N 1.75.

EXAMPLE 22

Preparation of (8S)-8-fluoroerythromycin A butyrate

Using the general method of the example 20 (8S)-8-fluoroerythromycin A was converted to (8S)-8-fluoroerythromycin A butyrate by esterification with butyraldehyde. The final product had the following characteristics:

m.p. 120°–5° C. (ethyl ether/n-hexane).
$[\alpha]_D^{20} -49°$ (C=1 in acetone)
IR (KBr): 3490, 1740, 1455, 1370, 1340, 1180 (shoulder), 1160, 1085, 1050, 1030, 1010, 995, 975, 955, 930, 890, 865, 830 cm$^{-1}$.

The analysis for $C_{41}H_{72}FNO_{14}$ gave the following results: calculated (%): C 59.91; H 8.83; F 2.31; N 1.70; found (%): C 60.13; H 8.71; F 2.27; N 1.75.

EXAMPLE 23

Preparation of (8S)-8-fluoroerythromycin A ethyl succinate.

Using the general process of the example 20 (8S)-8-fluoroerythromycine A was converted to (8S)-8-fluoroerythromycin A ethyl succinate by esterification with ethyl succinyl chloride. The final product showed the following characteristics:

m.p. 80°–85° C. (ethyl ether/n-hexane).
$[\alpha]_D^{20} -52.7°$ (C=1 in acetoe).
IR (KBr) 3480, 1735, 1450, 1370, 1345, 1190 (shoulder), 1160, 1050, 1030, 1010, 995, 975, 955, 890, 800 cm$^{-1}$.

The analysis for $C_{43}H_{74}FNO_{16}$ gave the following values: calculated (%): C 58.69; H 8.48; F 2.16; N 1.59; found (%): C 58.81; H 8.57; F 2.07; N 1.65.

EXAMPLE 24

Preparation of (8S)-8-fluoroeythromycin A succinate

A solution containing 7.520 g (0.010 moles) of (8S)-8-fluoroerythromycin A and 1 g (0.010 moles) of succinic anhydride in 37.5 mls of anhydrous acetone was heated to 80° C. for 15 minutes, cooled and maintained at room temperature for 2 hours. Then the procedure of the example 20 was adopted until a solid residue of 7.565 g was obtained. By crystallization of the solid from ethyl ether 6.450 g of (8S)-8-fluoroerythromycin A succinate were obtained having the following characteristics:

m.p. 150°–55° C.
$[\alpha]_D^{20} -52.7°$ (C=1 in acetone).
IR (KBr): 3450, 1730, 1575, 1455, 1370, 1340, 1190 (shoulder), 1160, 1050, 990 975, 950, 930, 885, 860, 825, 800 cm$^{-1}$.

The analysis for $C_{41}H_{70}FNO_{16}$ gave the following results: calculated (%): C 61.25; H 8.77; F 2.36; N 1.74; found (%): C 61.52; H 8.65; F 2.32; N 1.78.

EXAMPLE 25

Preparation of (8S)-8-fluoroerythromycin A lactobionate.

A solution of 3.4 g (0.010 moles) of δ-lactone of the lactiobionic acid in 20 mls of distilled water was added o a solution of 7.520 g (0.010 moles) of (8S)-8-fluoro-erythromycin A in 40 mls of acetone.

The resulting solution was evaporated under vacuum at 40° C. until a gummy residue was obtained. The residue was then dissolved in 50 mls of distilled water and the resulting solution was lyophilized. 10.6 g of (8S)-8-fluoroerythromycin A lactobionate were thus obtained having the following characteristics:

m.p. 145°-55° C.

IR (KBr): 3400 (broad), 1725, 1605, 1455 (shoulder), 1370, 1340 (shoulder), 1160, 1070, 1040, 1000, 950, 885 $cm^{-1}$.

The analysis for $C_{49}H_{88}FNO_{25}$ gave the following values: calculated (%): C 53.01; H 7.99; F 1.71; N 1.26; found (%): C 52.72; H 7.67; F 1.65; N 1.21.

EXAMPLE 26

Preparation of (8S)-8-fluoroerythromycin A stearate

A solution of 2.85 g (0.010 moles) of stearic acid in 20 mls of acetone-distilled water (1:1) was added to a solution of 7.520 g (0.010 moles) of (8S)-8-fluoroerythromycin A in 40 mls of acetone.

The resulting solution was then evaporated under vacuum until a solid residue was obtained which by crystallization from acetone/n-hexane gave 10.2 g of (8S)-8-fluoroerythromycin A stearate characterized by:

m.p. 100°-105° C.

IR (KBr): 3470, 1730, 1455, 1375, 1340, 1160, 1150, 1105, 1050, 1030, 1010, 990, 975, 950, 930, 890, 830, 800 $cm^{-1}$.

The analysis for $C_{55}H_{102}FNO_{15}$ gave the following results: calculated (%): C 63.74; H 9.92; F 1.83; N 1.35; found (%): C 63.37; H 9.81; F 1.69; N 1.27.

EXAMPLE 27

Preparation of (8S)-8-fluoroerythromycin A propionate laurylsulphate

A solution of 2.885 g (0.010 moles) of lauryl sulphate sodium salt in 50 mls of distilled water was added to a solution of 8.080 g (0.010 moles) of (8S)-8-fluoroerythromycin A propionate (prepared in the example 21) in 75 mls of acetone. Under electromagnetic stirring the thus obtained solution was then supplemented with 20 mls of a 5% aqueous solution of acetic acid. The resulting salt was filtered, washed several times with water and then dried at 50° C. under vacuum. 10.25 g of (8S)-8-fluoroerythromycin A propionate laurylsulphate were thus obtained.

The analysis for $C_{52}H_{96}FNO_{18}S$ gave the following results: calculated (%): C 58.13; H 9.01; F 1.77; N 1.30; S, 2.98; found (%): C 57.89; H 8.92; F 1.72; N 1.26; S 2.94.

EXAMPLE 28

Preparation of (8S)-8-fluoroerythromycin A carbonate

A solution of 7.045 g (0.080 moles) of ethylene carbonate in 20 mls of anhydrous benzene, already heated, was dropwise added (over about 1 hour) to a mixture of 7.520 g (0.010 moles) of (8S)-8-fluoroerythromycin A, 3.760 g of potassium carbonate and 20 mls of benzene, vigorously stirred and heated to reflux temperature. At the end of the addition the reaction mixture was heated to refluxing for further 15 minutes and cooled to room temperature. There were then added under stirring 40 mls of water.

The benzene phase was then separated, washed three times with watern dried over anhydrous $Na_2SO_4$ and then evaporated to dryness under vacuum at 50° C.

The residue was dissolved in ethyl ether and brought to dryness under vacuum. The latter operation was repeated some times and the resulting residue was then purified by chromatography in a silica gel column. The fractions containing only (8S)-8-fluoroerythromycin A carbonate were combined (the control being carried out by high pressure liquid phase chromatography).

The combined fractions 16 to 22, evaporated under vacuum to dryness and crystallized from ethyl ether, gave 0.980 g of (8S)-8-fluoroerythromycin A carbonate, having the following characteristics:

m.p. 234°-5° C.

$[\alpha]_D^{20} - 44.2°$ (C=1 in methanol).

IR (KBr); 3500, 3450, 1795, 1745, 1455, 1380, 1365, 1345, 1325, 1295, 1280, 1235, 1160, 1090, 1070, 1040, 1015, 1000, 990, 940, 930, 900, 875, 865, 830, 815, 800 $cm^{-1}$.

The analysis for $C_{38}H_{64}FNO_{14}$ gave the following values: calculated (%): C 58.67; H 8.29; F 2.44; N 1.80; found (%): C 58.41; H 7.80; F 2.40; N 1.71.

According to the same procedures there are prepared the salts, esters, and salt-esters corresponding to the other macrolide antibiotics of the invention.

The novel antibiotics of the present invention as well as the above mentioned related derivatives are used for the preparation of pharmaceutical compositions, mainly for the oral administration, which are obtained with the conventional pharmaceutical techniques and with the usual excipients, vehicles, fillers, etc.

There are thus contemplated tablets, pills, capsules, suspensions and solutions containing from 10 to 1000 mg of active ingredient per dose, whereas the daily dosages are those normally adopted for the analogous antibiotic, namely the erythromycin.

The following examples illustrate the preparation of compositions and formulations containing (8S)-8-fluoroerythromycin A, it being meant that it is likewise foreseen for the other macrolide antibiotcs of the present invention and that these examples shall not unduly limit the invention.

EXAMPLE 29

Capsules: doses for 1000 units
(8S)-8fluoroerythromycin A: g 100
magnesium stearate: g 3

Preparation

The above indicated substances are homogeneously mixed and capsules of hard gelatin are filled according to the usual technique.

The contents for capsule is 103 mg. Each capsule contains 100 mg of active ingredient.

EXAMPLE 30

Capsules: doses for 1000 units
(8S)-8-fluoroerythromycin A: g 250
magnesium stearate: g 7,5

Preparation

The same technique disclosed in the preceding example is repeated. Each capsule, containing 257 mg of powder mixture, corresponds to 250 mg of active ingredient.

EXAMPLE 31

Capsules: doses for 1000 units
(8S)-8-fluoroerythromycin A: g 500
magnesium stearate: g 15

The same technique described in the preceding example is repeated.

Each capsule, containing 515 mg of powder mixture, correspond to 500 mg of active substance.

EXAMPLE 32

Tablets: doses for 1000 units
(8S)-8-fluoroerythromycin A: g 100
corn starch: g 50
lactose: g 30
talc: g 8
magnesium stearate: g 2
hydroxypropylmethylcellulose: g 6
ethylcellulose: g 4

Preparation (8S)-8-fluoroerythromycin A, part of the starch and the lactose are homogeneously mixed and the granulation is effected, according to the technique of the moist granulation, using as the bonding agent the remaining amount of starch in form of starch-water.

The dried granulate is mixed with lubricants and the compression is carried out.

Tablets are obtained having 190 mg weight. Each tablets contains 100 mg of active substance.

The tablets can be charged in a coating basin and film coated by means of a solution of hydroxypropylmethylcellulose and ethylcellulose. The weight of the finished tablets is 200 mg.

EXAMPLE 33

Tablets: doses for 1000 units
(8S)-8fluoroerythromycin A: g 250
corn starch: g 70
lactose: g 40
talc: g 16
magnesium stearate: g 4
hydroxypropylmethylcellulose: g 12
ethylcellulose: g 8

Preparation

The technique described in the preceding example is repeated.

Each tablet of the weight of 400 mg contains 250 mg of active substance.

EXAMPLE 34

Tablets: doses for 1000 units
(8S)-8-fluoroerythromycin A: g 500
corn starch: g 140
lactose: g 85
talc: g 37
magnesium stearate: g 8
hydroxypropylmethylcellulose: g 18
ethylcellulose: g 12

The same technique described in the preceding example is repeated.

Each tablet of the weight of 800 mg contains 500 mg of active substance.

EXAMPLE 35

Extemporary suspension: 60 mls of suspension
(8S)-8-fluoroerythromycin A: g 0.6
sodium carboxymethylcellulose: g 0.010
methyl p-hydroxybenzoate: g 0.048
propyl p-hydroxybenzoate: g 0.012
flavoring agents: g 0.600
sucrose powder: to a total weight of g 30

Preparation

The ingredients are intimately admixed and charged in a 60 ml calibrated bottle. Before the use the bottle is filled with water to obtain 60 mls of suspension, which are well stirred before the use. The reformed suspension contains 10 mg/ml of active substance.

EXAMPLE 36

Extemporary suspension: doses for 60 mls of suspension
(8S)-8-fluoroerythromycin A: g 3
carboxymethylcellulose: g 0.010
methyl p-hydroxybenzoate: g 0.048
propyl p-hydroxybenzoate: g 0.012
flavoring agents: g 0.600
sucrose to form a total weight of 30 g Preparation The same technique described in the preceding example is repeated. The suspension reconstituted contains 50 mg/ml of active substance.

EXAMPLE 37

Drops: doses for 10 mls
(8S)-8-fluoroerythromycin A: g 0.5
methyl p-hydroxybenzoate: g 0.09
propyl p-hydroxybenzoate: g 0.01
hydroxyethylcellulose: g 0.050
glycerine: g 0.400
sweetening and flavoring agents: g 0.100
depurated water: to form 10 mls In a suitable container provided with a mechanical stirrer 90% of the water needed for the preparation is charged and heated to 80° C.

Thereinto are dissolved the parasepticals and subsequently the hydroxyethylcellulose.

Under stirring the other components are added and 10 ml vials are filled. The thus obtained suspension has a content of 50 mg/ml of active substance.

EXAMPLE 38

Drops: doses for 10 mls
(8S)-8-fluoroerythromycin A: g 2.500
methyl p-hydroxybenzoate: g 0.009
propyl p-hydroxybenzoate: g 0.001
hydroxyethylcellulose: g 0.050
glycerine: g 0.400
sweetening and flavoring agents: g 0.100
depurated water: to form 10 mls Preparation The same technique described in the preceding example is repeated. Each ml of the suspension contains 250 mg of active substance.

EXAMPLE 39

Capsules: doses for 1000 units
(8S)-8-fluoroerythromycin A propionate lauryl sulphate (corresponding to 100 g of (8S)-8-fluoroerythromycin A): g 142.9
magnesium stearate: g 4.1

Preparation

The same technique described in the preceding example 29 is repeated. The contents of each capsule is 147 mg. Each capsule contains (8S)-8-fluoroerythromycin A propionate laurylsulphate corresponding to 100 mg of (8S)-8-fluoroerythromycin A.

EXAMPLE 40

Capsules: doses for 1000 units
(8S)-8-fluoroerythromycin A propionate lauryl sulphate (corresponding to 250 g of (8S)-8-fluoroerythromycin A): g 357.2
magnesium stearate: g 10.8

Preparation

The same technique described in the preceding example is repeated. Each capsule, containing 368 mg of powder mixture, contains 357.2 mg of (8S)-8-fluoroerythromycin A propionate lauryl sulphate corresponding to 250 mg of (8S)-8-fluoroerythromycin A.

EXAMPLE 41

Tablets: doses for 1000 units
(8S)-8-fluoroerythromycin A stearate (corresponding to 100 g of (8S)-8-fluoroerythromycin A): g 137.83
corn starch: g 55.00
lactose: g 32.50
talc: g 10.00
magnesium stearate: g 2.17
hydroxypropylmethylcellulose: g 7.50
ethyl cellulose: g 5.00

Preparation

The same technique described in the preceding example 32 is used. Tablets are obtained having a weight of 240 mg. Each tablet contains 137.83 mg of (8S)-8-fluoroerythromycin A stearate, corresponding to 100 mg of (8S)-8-fluoroerythromycin A.

The tablets are charged in a shallow basin and film coated by means of a solution of hydroxypropylmethylcellulose and ethyl cellulose. The weight of the finished tablets is 250 mg.

EXAMPLE 42

Tablets: doses per 1000 units
(8S)-8-fluoroerythromycin A stearate (corresponding to 500 g of (8S)-8-fluoroerythromycin A): g 689.17
corn starch: g 150.00
lactose: g 80.00
talc: g 40.83
magnesium stearate: g 10.00
hydroxypropylmethylcellulose: g 18.00
ethylcellulose: g 12.00

Preparation

The same technique described in the preceding example 32 is used. Each tablet of the weight of 1 g contains 689.17 mg of (8S)-8-fluoroerythromycin A stearate, corresponding to 500 mg of (8S)-8-fluoroerythromycin A.

EXAMPLE 43

Extemporary suspension: 60 mls of suspension
(8S)-8-fluoroerythromycin A ethylsuccinate (corresponding to 0.6 g of (8S)-8-fluoroerythromycin A): g 0.702
sodium carboxymethylcellulose: g 0.010
methyl p-hydroxybenzoate: g 0.048
propyl p-hydroxybenzoate: g 0.012
flavoring agents: g 0.600
sucrose: to form 30 g Preparation The same technique described in the example 35 is used,. The reconstituted suspension contains (8S)-8-fluoroerythromycin A ethylsuccinate corresponding to 10 mg/ml of (8S)-8-fluoroerythromycin A.

EXAMPLE 44

Vials for i.v. use: doses for 1000 units 738 g of (8S)-8-fluoroerythromycin A lactobionate, corresponding to 500 g of (8S)-8-fluoroerythromycin A, are dissolved in water and after sterile filtration, are lyophilized. The obtained product is subdivided in a sterile environment in glass vials each containing 738 mg (corresponding to 500 mg of (8S)-8-fluoroerythromycin A).

The macrolide antibiotics of the present invention have been investigated by pharmacological tests aiming to determine:

the bacteriostatic power, expressed as the minimum inhibiting concentration (MIC) against both aerobic and anaerobic, Gram positive and Gram negative, bacterial stocks: the related results are reported in the tables 2 and 3.

the serum concentrations relating to (8S)-8-fluoroerythromycin A and to the erythromycin A (table 4).

the bacterial power, expressed as the minimum bactericidal power (MBC) against some Gram positive aerobic stocks (table 5).

TABLE 2

Bacteriostatic power in solid medium of Erythromycin A, Erythromycin B, Oleandomycin, P-80202, P-80203, P-80204, P-80205, P-80206, P-80207 and P-80206 carbonate against aerobic and anaerobic, Gram positive and Gram negative bacteria. Minimum inhibiting concentrations expressed in mcg/ml.

| MICROORGANISM | Product | Erythromycin A | Erthromycin B | Oleandomycin | P80206 | P80203 | P80205 | P80202 | P80207 | P80204 | P80206 carbonate |
|---|---|---|---|---|---|---|---|---|---|---|---|
| 1. Aerobic |
| A. Gram positive |
| Staphylococcus aureus ATCC 6538P | LRP 39 | 0.049 | 0.097 | 0.39 | 0.097 | 0.097 | 0.097 | 0.097 | 0.39 | 0.39 | 0.097 |
| Staphylococcus aureus ATCC 6538P | LRP 14** | 0.049 | 0.195 | 0.39 | 0.097 | 0.097 | 0.097 | 0.097 | 0.39 | 0.39 | 0.097 |
| Staphylococcus aureus ATCC 14154 | LRP 78* | 25 | 25 | 25 | 25 | 25 | 25 | 25 | 25 | 25 | 25 |
| Streptococcus faecalis | LRP 7 | 0.097 | 0.195 | 1.56 | 0.195 | 0.195 | 0.097 | 0.097 | 0.39 | 0.39 | 0.097 |
| Streptococcus faecalis subsp. zymogenes |
| Streptococcus faecalis ATCC 12958 | LRP 61 | 0.097 | 0.195 | 1.56 | 0.195 | 0.195 | 0.097 | 0.097 | 0.39 | 0.39 | 0.097 |
| Streptococcus pneumoniae ATCC 6303 | LRP 35 | 0.012 | 0.024 | 0.195 | 0.024 | 0.049 | 0.024 | 0.024 | 0.049 | 0.049 | 0.012 |
| Streptococcus pneumoniae ATCC 6303 | LRP 52 | 0.012 | 0.024 | 0.195 | 0.024 | 0.024 | 0.012 | 0.024 | 0.049 | 0.049 | 0.012 |

TABLE 2-continued

Bacteriostatic power in solid medium of Erythromycin A, Erythromycin B, Oleandomycin, P-80202, P-80203, P-80204, P-80205, P-80206, P-80207 and P-80206 carbonate against aerobic and anaerobic, Gram positive and Gram negative bacteria. Minimum inhibiting concentrations expressed in mcg/ml.

| MICROORGANISM | Product | Erythromycin A | Erthromycin B | Oleandomycin | P80206 | P80203 | P80205 | P80202 | P80207 | P80204 | P80206 carbonate |
|---|---|---|---|---|---|---|---|---|---|---|---|
| Streptococcus pneumoniae ATCC 6303 | LRP 53 | 0.012 | 0.024 | 0.195 | 0.024 | 0.024 | 0.024 | 0.024 | 0.097 | 0.049 | 0.012 |
| Streptococcus pyogenes ATCC 8668 | LRP 34 | 0.012 | 0.024 | 0.195 | 0.012 | 0.024 | 0.024 | 0.024 | 0.049 | 0.049 | 0.012 |
| Streptococcus pyogenes ATCC 8668 | LRP 197 | 0.012 | 0.024 | 0.195 | 0.012 | 0.049 | 0.024 | 0.024 | 0.097 | 0.049 | 0.024 |
| Corynebacterium diphteriae | LRP 24 | 0.006 | 0.012 | 0.097 | 0.012 | 0.006 | 0.012 | 0.006 | 0.049 | 0.049 | 0.024 |
| Micrococcus luteus ATCC 9341 | LRP 6 | 0.006 | 0.006 | 0.049 | 0.006 | 0.012 | 0.012 | 0.006 | 0.049 | 0.049 | 0.024 |
| Micrococcus luteus ATCC 15957 | LRP 193* | 25 | 25 | 25 | 25 | 25 | 25 | 25 | 25 | 25 | 25 |
| Bacillus subtilis | LRP 25 | 0.049 | 0.049 | 0.39 | 0.049 | 0.049 | 0.097 | 0.049 | 0.39 | 0.195 | 0.049 |
| B. Gram negative | | | | | | | | | | | |
| Haemophilus influenzae ATCC 19418 | LRP 213 | 3.12 | 6.25 | 25 | 3.12 | 6.25 | 12.5 | 6.25 | 12.5 | 6.25 | 6.25 |
| Neisseria gonorrhoeae ATCC 19424 | LRP 214 | 0.049 | 0.097 | 0.39 | 0.049 | 0.097 | 0.195 | 0.097 | 0.097 | 0.39 | 0.049 |
| Escherichia coli | LRP 50 | 6.25 | 25 | 25 | 12.5 | 25 | 12.5 | 25 | 25 | 25 | 3.12 |
| Klelsiella pneumoniae | LRP 54 | 12.5 | 25 | 25 | 12.5 | 25 | 25 | 25 | 25 | 25 | 12.5 |
| Proteus vulgaris ATCC 6380 | LRP 13 | 25 | 25 | 25 | 25 | 25 | 25 | 25 | 25 | 25 | 25 |
| Pseudomonas aeruginosa | LRP 9 | 25 | 25 | 25 | 25 | 25 | 25 | 25 | 25 | 25 | 25 |
| Salmonella typhy | LRP 8 | 12.5 | 25 | 25 | 12.5 | 25 | 12.5 | 12.5 | 25 | 25 | 12.5 |
| Shigella sonnei | LRP 5 | 12.5 | 25 | 25 | 25 | 25 | 25 | 25 | 25 | 25 | 12.5 |
| Acholeplasma laidlawii ATCC 23206 | LRP 204 | 0.097 | 0.097 | 6.25 | 0.097 | 0.195 | 3.12 | 3.12 | 3.12 | 3.12 | 0.195 |
| Mycoplasma hominis I ATCC 14027 | LRP 211 | 25 | 25 | 25 | 25 | 25 | 25 | 25 | 25 | 25 | 25 |
| 2. Anaerobic | | | | | | | | | | | |
| Clostridium perfrigens ATCC 3624 | LRP 206 | 1.56 | 1.56 | 3.12 | 0.78 | 0.39 | 6.25 | 3.12 | 6.25 | 1.56 | 3.12 |
| Bacteroides fragilis ATCC 23745 | LRP 205 | 0.195 | 0.195 | 0.39 | 0.195 | 0.195 | 0.78 | 0.39 | 3.12 | 3.12 | 0.78 |
| Fusobacteriumnecrophroum ATCC 27852 | LRP 210 | 3.12 | 6.25 | 6.25 | 1.56 | 3.12 | 12.5 | 6.25 | 12.5 | 12.5 | 6.25 |

Legenda:
*Erythromycin resistant
**Penycilline resistant

TABLE 3

Bacteriostatic power in liquid medium of Erithromycin A, Erithromycin B, Oleandomycin, P 80202, P 80203, P 80204, P 80205, P 80206, P 80207 and P 80206 carbonate on few Gram positive aerobic bacteria. Minimum inhibiting concentrations expressed in mcg/ml

| MICROORGANISM | Product | Erithromycin A | Erithromycin B | Oleandomycin | P80206 | P80203 | P80205 | P80202 | P80207 | P80204 | P80206 carbonate |
|---|---|---|---|---|---|---|---|---|---|---|---|
| Staphylococcus aureus ATCC 6538 P | LRP 39 | 0.097 | 0.195 | 0.39 | 0.195 | 0.097 | 0.195 | 0.195 | 0.78 | 0.195 | 0.39 |
| Streptococcus faecalis subs. zymogenes ATCC 12958 | LRP 61 | 0.39 | 0.39 | 1.56 | 0.39 | 0.39 | 0.39 | 0.39 | 0.78 | 0.39 | 0.195 |
| Streptococcus pneumoniae ATCC 6303 | LRP 35 | 0.024 | 0.049 | 0.195 | 0.049 | 0.049 | 0.097 | 0.049 | 0.049 | 0.024 | 0.049 |
| Streptococcus pyogenes ATCC 8668 | LRP 34 | 0.024 | 0.024 | 0.195 | 0.097 | 0.024 | 0.049 | 0.049 | 0.097 | 0.049 | 0.024 |
| Corynebacterium diphteriae | LRP 24 | 0.012 | 0.012 | 0.097 | 0.012 | 0.012 | 0.049 | 0.012 | 0.049 | 0.024 | 0.024 |

TABLE 4

Serum concentrations of P 80206 and Erythromycin A base in the rat after administration of 100 mg/kg per os. The values, at the several sampling times, correspond to mcg of product per ml of serum*.

| | P 80206 Sampling time (hours) | | | | | Erythromycin base sampling time (hours) | | | | |
|---|---|---|---|---|---|---|---|---|---|---|
| | 0.5 | 1 | 2 | 4 | 6 | 0.5 | 1 | 2 | 4 | 6 |
| | 0.078 | 8.505 | 3.712 | 1.792 | 0.867 | 0.016 | 1.542 | 1.332 | 0.075 | 0.112 |
| | 0.198 | 0.880 | 6.516 | 2.134 | 0.393 | 0.010 | 0.102 | 2.205 | 0.540 | 0.245 |
| | 0.630 | 1.273 | 3.510 | 1.270 | 1.192 | 0.063 | 0.090 | 0.220 | 0.117 | 0.010 |
| | 0.487 | 1.251 | 6.907 | 2.817 | 1.792 | 0.387 | 0.285 | 0.830 | 0.499 | 0.246 |
| | 1.105 | 1.714 | 6.601 | 2.362 | 1.620 | 1.545 | 0.503 | 0.360 | 0.198 | 0.246 |
| | 1.333 | 0.531 | 7.195 | 2.115 | 1.147 | 0.849 | 0.686 | 1.878 | 0.144 | 0.135 |
| Average | 0.638 | 2.359 | 5.740 | 2.081 | 1.168 | 0.478 | 0.534 | 1.137 | 0.262 | 0.165 |
| Standard error | 0.2026 | 1.240 | 0.680 | 0.213 | 0.207 | 0.250 | 0.222 | 0.330 | 0.083 | 0.039 |
| Reliability lower | 0.118 | −0.829 | 3.990 | 1.533 | 0.636 | −0.167 | −0.038 | 0.289 | 0.048 | 0.064 |
| Limits upper | 1.159 | 5.547 | 7.491 | 2.630 | 1.701 | 1.123 | 1.107 | 1.986 | 0.476 | 0.268 |

*The serums of the rats at the 0 time did not show antibacterial activity.

TABLE 5

Bacterial power of Erythromycin A, Erythromycin B, Oleandomycin,
P 80202, P 80203, P 80204, P 80205, P 80206,
P 80207 and P 80206 carbonate against some Gram Positive aerobic stocks.
Minimum bactericidal concentrations (MBC), expressed in mcg/ml.

| MICROORGANISM | Erithromcyn A | MBC/MIC | Erithromcyn B | MBC/MIC | Oleandomycyn | MBC/MIC | P80206 | MBC/MIC | P80203 | MBC/MIC |
|---|---|---|---|---|---|---|---|---|---|---|
| Staphylococcus aureus ATCC 6538 P LRP 39 | 1.56 | 16 | 6.25 | 32 | 6.25 | 16 | 3.12 | 16 | 3.12 | 32 |
| Streptococcus faecalis subs. zymogenes LRP 61 | 6.25 | 16 | 6.25 | 16 | >12.5 | >8 | 6.25 | 16 | 3.12 | 8 |
| Streptococcus pneumoniae ATCC 6303 LRP 35 | 0.097 | 4 | 0.195 | 4 | 0.78 | 4 | 0.195 | 4 | 0.049 | 1 |
| Streptococcus pyogenes ATCC 8668 LRP 34 | 0.39 | 16 | 0.195 | 8 | 3.12 | 16 | 0.78 | 8 | 0.195 | 8 |
| Corynebacterium diphteriae LRP 24 | 0.049 | 4 | 0.195 | 16 | 0.39 | 4 | 0.097 | 8 | 0.049 | 4 |

| MICROORGANISM | P80205 | MBC/MIC | P80202 | MBC/MIC | P80207 | MBC/MIC | P80204 | MBC/MIC | P80206 | MBC/MIC |
|---|---|---|---|---|---|---|---|---|---|---|
| Staphylococcus aureus ATCC 6538 P LRP 39 | 3.12 | 16 | 3.12 | 16 | 6.25 | 8 | 3.12 | 16 | 6.25 | 16 |
| Streptococcus faecalis subs. zymogenes LRP 61 | >3.12 | >8 | 3.12 | 8 | 6.25 | 8 | 6.25 | 16 | 3.12 | 16 |
| Streptococcus pneumoniae ATCC 6303 LRP 35 | 0.195 | 2 | 0.195 | 4 | 0.097 | 2 | 0.049 | 2 | 0.195 | 4 |
| Streptococcus pyogenes ATCC 8668 LRP 34 | 0.78 | 16 | 0.39 | 8 | 0.78 | 8 | 0.39 | 8 | 0.39 | 16 |
| Corynebacterium diphteriae LRP 24 | 0.39 | 8 | 0.195 | 16 | 0.195 | 4 | 0.39 | 16 | 0.39 | 16 |

Legenda:
n.d. = not determined

We claim:

1. (8S)-8-fluoroerythronolide A, having the formula:

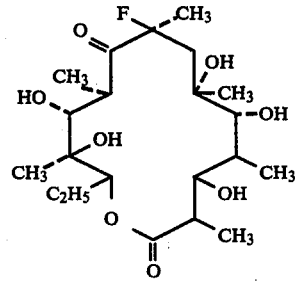

2. (8S)-8-fluoroerythronolide A-6,9;9,11-acetal, having the formula:

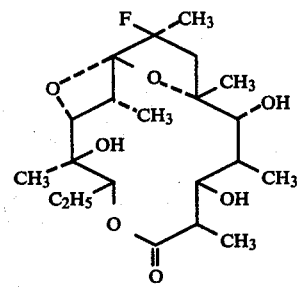

3. 8,9-anhydroerythronolide A 6,9-hemiacetal, having the formula:

4. (8S)-8-fluoroerythronolide B, having the formula:

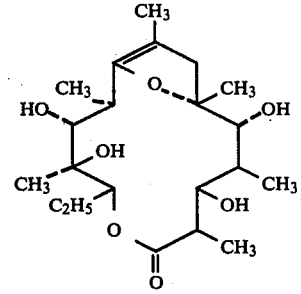

5. (8S)-8-fluoroerythronolide B-6,9;9,11-acetal, having the formula:

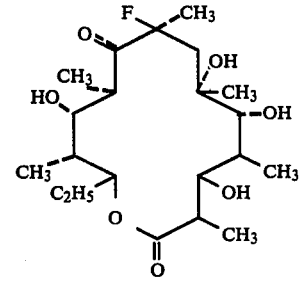

6. 3-O-mycarosyl-(8S)-8-fluoroerythronolide B, having the formula:

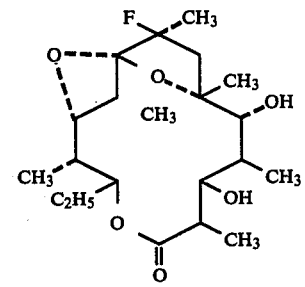

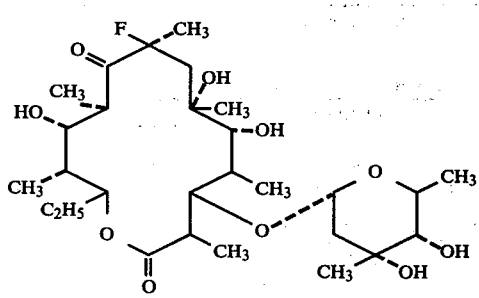

7. 3-O-mycarosyl-(8S)-8-fluoroerythrnolide B-6,9;9,11-acetal having the formula:

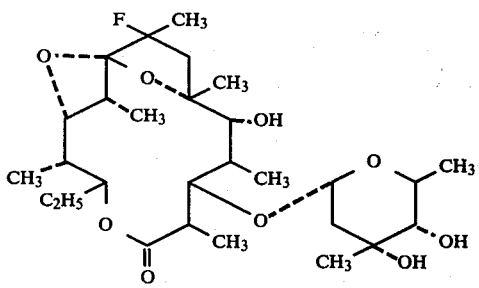

8. 3-O-mycarosyl-8,9-anhydroerythronolide B-6,9-hemiacetal having the formula:

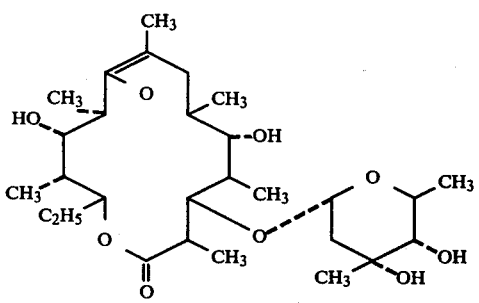

9. (8S)-8-fluoroerythromycin A, having the formula

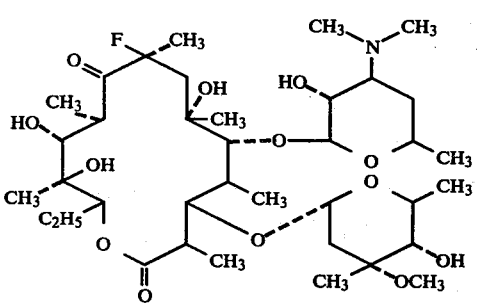

or the pharmaceutically acceptable salts thereof.

10. (8S)-8-fluoroerythromycin B, having the formula

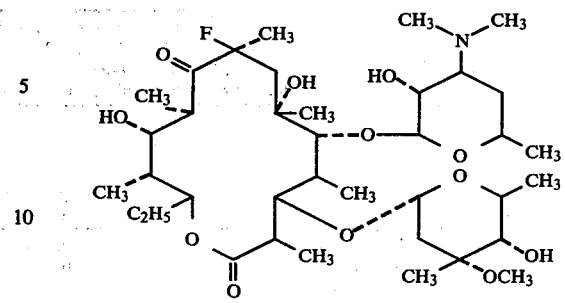

or the pharmaceutically acceptable salts thereof.

11. (8S)-8-fluoroerythromycin C, having the formula

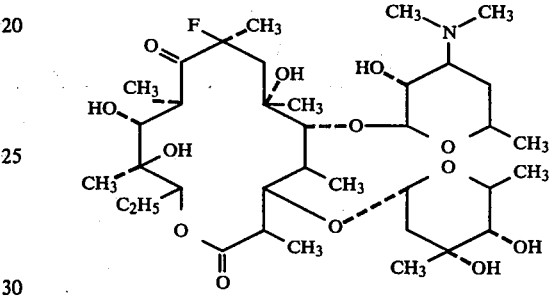

or the pharmaceutically acceptable salts thereof.

12. (8S)-8-fluoroerythromycin D, having the formula

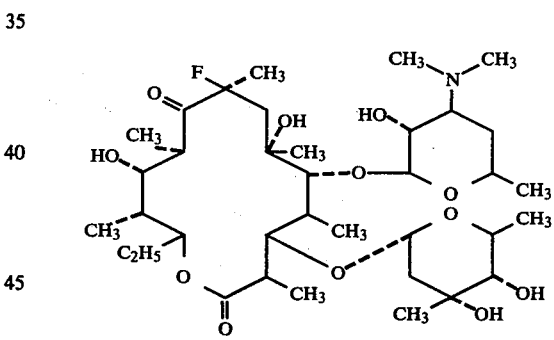

or the pharmaceutically acceptable salts thereof.

13. 3-O-oleandrosyl-5-O-desosaminyl-(8s)-8-fluoroerythronolide A, having the formula

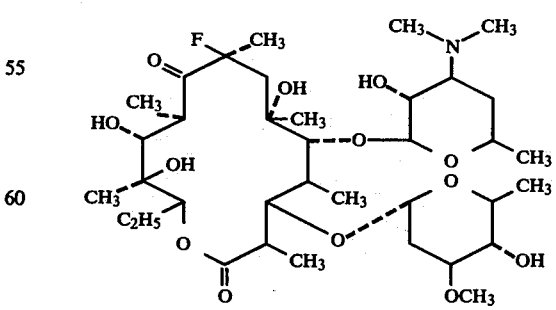

or the pharmaceutically acceptable salts thereof.

14. 3-O-oleandrosyl-5-O-desosaminyl-(8S)-8-fluoroerythronolide B, having the formula

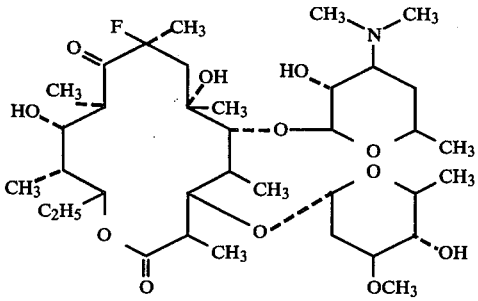

or the pharmaceutically acceptable salts thereof.

15. Compounds according to claim 9, 11 or 13 in the form of the carbonate salt.

16. Pharmaceutical composition containing an antibiotic-effective amount of a compound of any one of claims 9, 10, 11, 12, 13 or 14 with a pharmaceutically acceptable excipient therefor.

17. Composition of claim 16, wherein said composition is in a form suitable for oral administration.

18. Composition according to claim 16, wherein said amount is between 10 and 1000 mg of said compound.

19. A pharmaceutically acceptable ester or salt-ester of the compound as claimed in claim 9, 10, 11, 12, 13 or 14.

20. A compound as claimed in claim 19 selected from the group consisting of
(8S)-8-fluoroerythromycin A acetate,
(8S)-8-fluoroerythromycin A propionate,
(8S)-8-fluoroerythromycin A butyrate,
(8S)-8-fluoroerythromycin ether succinate,
(8S)-8-fluoroerythromycin A succinate,
(8S)-8-fluoroerythromycin A lactobionate,
(8S)-8-fluoroerythromycin A stearate,
(8S)-8-fluoroerythromycin A propionate laurylsulphate, and
(8S)-8-fluoroerythromycin A carbonate.

21. A compound as claimed in claim 19 selected from the group consisting of
(8S)-8-fluoroerythromycin B acetate,
(8S)-8-fluoroerythromycin B propionate,
(8S)-8-fluoroerythromycin B butyrate,
(8S)-8-fluoroerythromycin B ethyl succinate,
(8S)-8-fluoroerythromycin B succinate,
(8S)-8-fluoroerythromycin B lactobionate,
(8S)-8-fluoroerythromycin B stearate,
(8S)-8-fluoroerythromycin B propionate laurylsulphate, and
(8S)-8-fluoroerythromycin B carbonate.

22. A compound as claimed in claim 19 selected from the group of
(8S)-8-fluoroerythromycin C acetate,
(8S)-8-fluoroerythromycin C propionate,
(8S)-8-fluoroerythromycin C butyrate,
(8S)-8-fluoroerythromycin C ethyl succinate,
(8S)-8-fluoroerythromycin C succinate,
(8S)-8-fluoroerythromycin C lactobionate,
(8S)-8-fluoroerythromycin C stearate,
(8S)-8-fluoroerythromycin C propionate laurylsulphate, and
(8S)-8-fluoroerythromycin C carbonate.

23. A compound as claimed in claim 19 selected from the group consisting of
(8S)-8-fluoroerythromycin D acetate,
(8S)-8-fluoroerythromycin D propionate,
(8S)-8-fluoroerythromycin D butyrate,
(8S)-8-fluoroerythromycin D ethyl succinate,
(8S)-8-fluoroerythromycin D succinate,
(8S)-8-fluoroerythromycin D lactobionate,
(8S)-8-fluoroerythromycin D stearate,
(8S)-8-fluoroerythromycin D propionate laurylsulphate, and
(8S)-8-fluoroerythromycin D carbonate.

24. A compound as claimed in claim 19 selected from the group consisting of
3-O-oleandrosyl-5-O-desoaminyl-(8S)-8-fluoroerythronolide A propionate,
3-O-oleandrosyl-5-O-desoaminyl-(8S)-8-fluoroerythronolide A butyrate,
3-O-oleandrosyl-5-O-desoaminyl-(8S)-8-fluoroerythronolide A ethyl succinate,
3-O-oleandrosyl-5-O-desoaminyl-(8S)-8-fluoroerythronolide A succinate,
3-O-oleandrosyl-5-O-desoaminyl-(8S)-8-fluoroerythronolide A lactobionate,
3-O-oleandrosyl-5-O-desoaminyl-(8S)-8-fluoroerythronolide A stearate,
3-O-oleandrosyl-5-O-desoaminyl-(8S)-8-fluoroerythronolide A propionate laurylsulphate, and
3-O-oleandrosyl-5-O-desoaminyl-(8S)-8-fluoroerythronolide A carbonate.

25. A compound as claimed in claim 19 selected from the group consisting of
3-O-oleandrosyl-5-O-desoaminyl-(8S)-8-fluoroerythronolide B acetate,
3-O-oleandrosyl-5-O-desoaminyl-(8S)-8-fluoroerythronolide B propionate,
3-O-oleandrosyl-5-O-desoaminyl-(8S)-8-fluoroerythronolide B butyrate,
3-O-oleandrosyl-5-O-desoaminyl-(8S)-8-fluoroerythronolide B ethyl succinate,
3-O-oleandrosyl-5-O-desoaminyl-(8S)-3-fluoroerythronolide B succinate,
3-O-oleandrosyl-5-O-desoaminyl-(8S)-8-fluoroerythronolide B lactobionate,
3-O-oleandrosyl-5-O-desoaminyl-(8S)-8-fluoroerythronolide B stearate,
3-O-oleandrosyl-5-O-desoaminyl-(8S)-8-fluoroerythronolide B propionate laurylsulphate, and
3-O-oleandrosyl-5-O-desoaminyl-(8S)-8-fluoroerythronolide B carbonate.

* * * * *

UNITED STATES PATENT AND TRADEMARK OFFICE
CERTIFICATE OF CORRECTION

PATENT NO. : 4,439,426

DATED : March 27, 1984

INVENTOR(S) : Luciano TOSCANO et al

It is certified that error appears in the above-identified patent and that said Letters Patent is hereby corrected as shown below:

In the Abstract, first paragraph, line 9, delete "3-0-mycarosyl-(8S)-fluoroerythronolide B" and insert therefor -- 3-0-mycarosyl-(8S)-8-fluoroerythronolide B --

In the Abstract, second paragraph, line 2, delete "convention" and insert therefor -- conversion --.

In the Abstract, second paragraph, lines 3-4, delete "hermiacetal" and insert therefor -- hemiacetal -- .

In column 2, Table 1, in the second vertical column of data, delete "100" in each of the last two rows labelled "$t\ 1/2$ (hours)" and insert therefor -- >100 -- in each instance.

In column 2, Table 1, in the third vertical column of data, delete "100" in each of the last six rows labelled "$t\ 1/2$ (hours)" and insert -- >100 -- .

UNITED STATES PATENT AND TRADEMARK OFFICE
CERTIFICATE OF CORRECTION

PATENT NO. : 4,439,426
DATED : March 27, 1984
INVENTOR(S) : Luciano Toscano et al It is certified that error appears in the above-identified patent and that said Letters Patent is hereby corrected as shown below:

Col. 3, delete lines 5-33 in their entirety and insert therefor

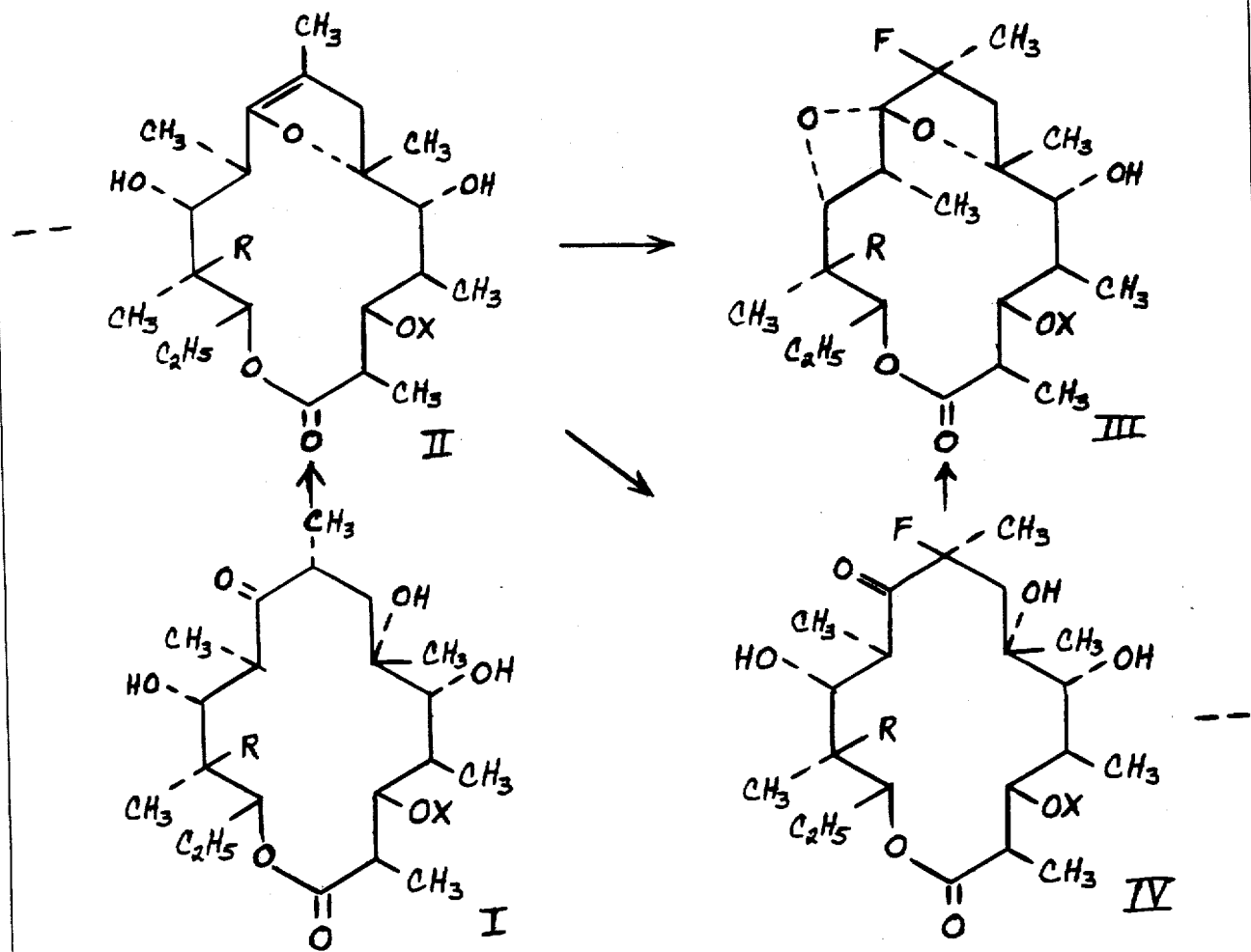

UNITED STATES PATENT AND TRADEMARK OFFICE
CERTIFICATE OF CORRECTION

PATENT NO. : 4,439,426   Page 3 of 11
DATED : March 27, 1984
INVENTOR(S) : Luciano Toscano et al It is certified that error appears in the above-identified patent and that said Letters Patent is hereby corrected as shown below:

Col. 4, delete lines 55-65 in their entirety and insert therefor

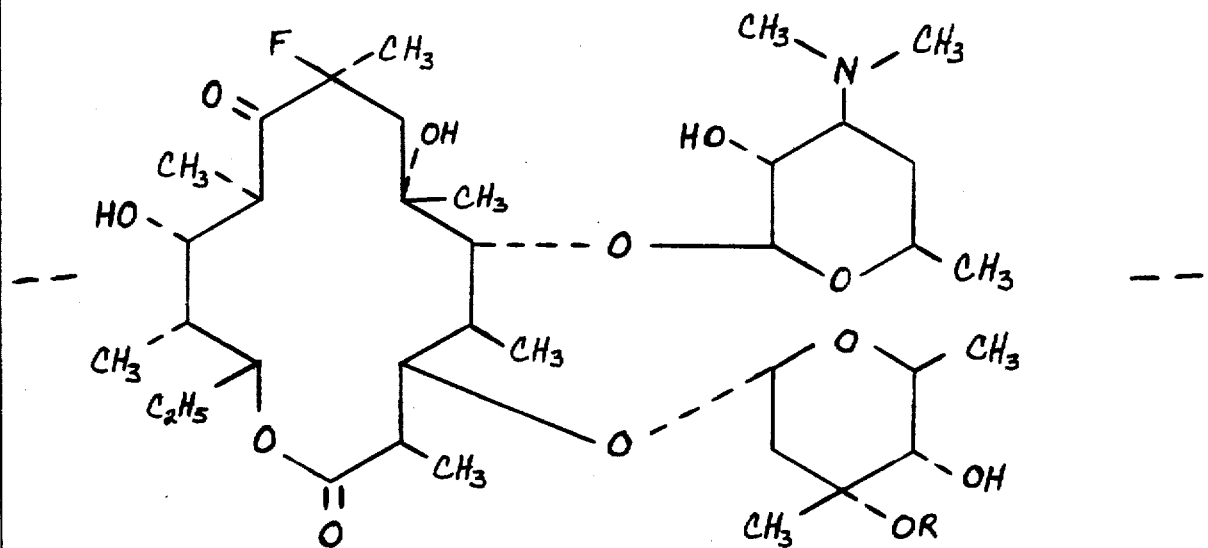

UNITED STATES PATENT AND TRADEMARK OFFICE
CERTIFICATE OF CORRECTION

PATENT NO. : 4,439,426
DATED : March 27, 1984
INVENTOR(S) : Luciano Toscano et al It is certified that error appears in the above-identified patent and that said Letters Patent is hereby corrected as shown below:

Col. 5, delete lines 1-13 in their entirety and insert therefor

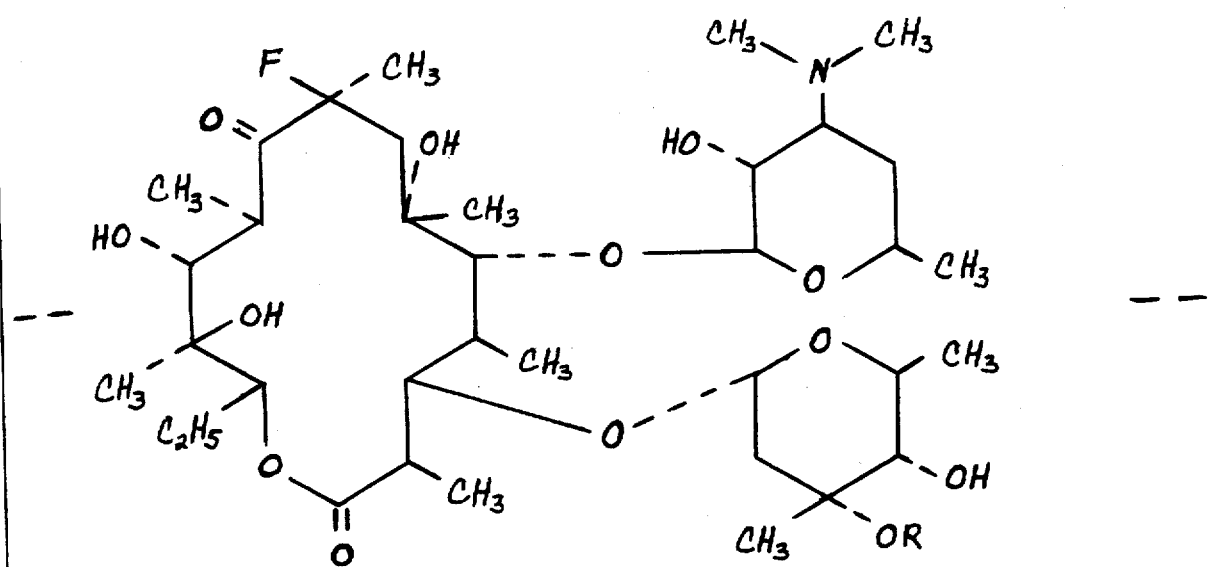

UNITED STATES PATENT AND TRADEMARK OFFICE
CERTIFICATE OF CORRECTION

PATENT NO. : 4,439,426  
DATED : March 27, 1984  
INVENTOR(S) : Luciano Toscano et al Page 5 of 11

It is certified that error appears in the above-identified patent and that said Letters Patent is hereby corrected as shown below:

Col. 5, line 22, after "31771", delete "which" and insert therefor -- . This -- ;

still line 22, after "respectively", delete -- to -- ;

line 25, before "oleandomycin", delete "the";

line 27, after "A, and", delete "to" ; and line 30, after "erythromycin", insert -- B when the substrate -- .

UNITED STATES PATENT AND TRADEMARK OFFICE
CERTIFICATE OF CORRECTION

PATENT NO. : 4,439,426

DATED : March 27, 1984

INVENTOR(S) : Luciano Toscano et al

Page 6 of 11

It is certified that error appears in the above-identified patent and that said Letters Patent is hereby corrected as shown below:

Col. 5, delete lines 34-45 in their entirety and insert therefor

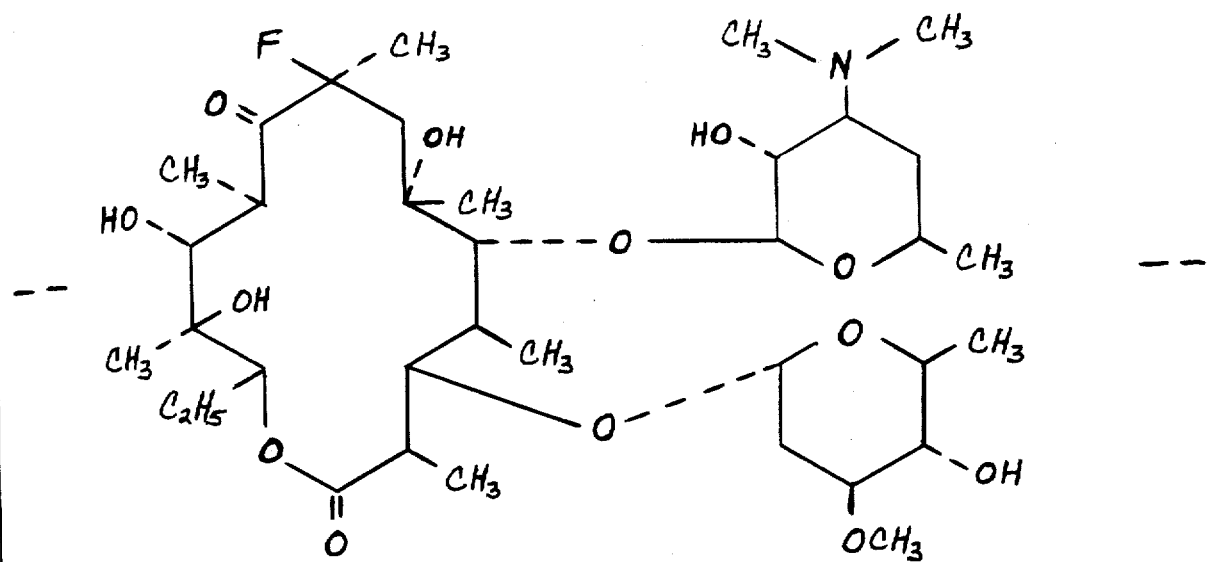

UNITED STATES PATENT AND TRADEMARK OFFICE
CERTIFICATE OF CORRECTION

PATENT NO. : 4,439,426

DATED : March 27, 1984

INVENTOR(S) : Luciano Toscano et al

Page 7 of 11

It is certified that error appears in the above-identified patent and that said Letters Patent is hereby corrected as shown below:

Col. 5, delete lines 50-62 in their entirety and insert therefor

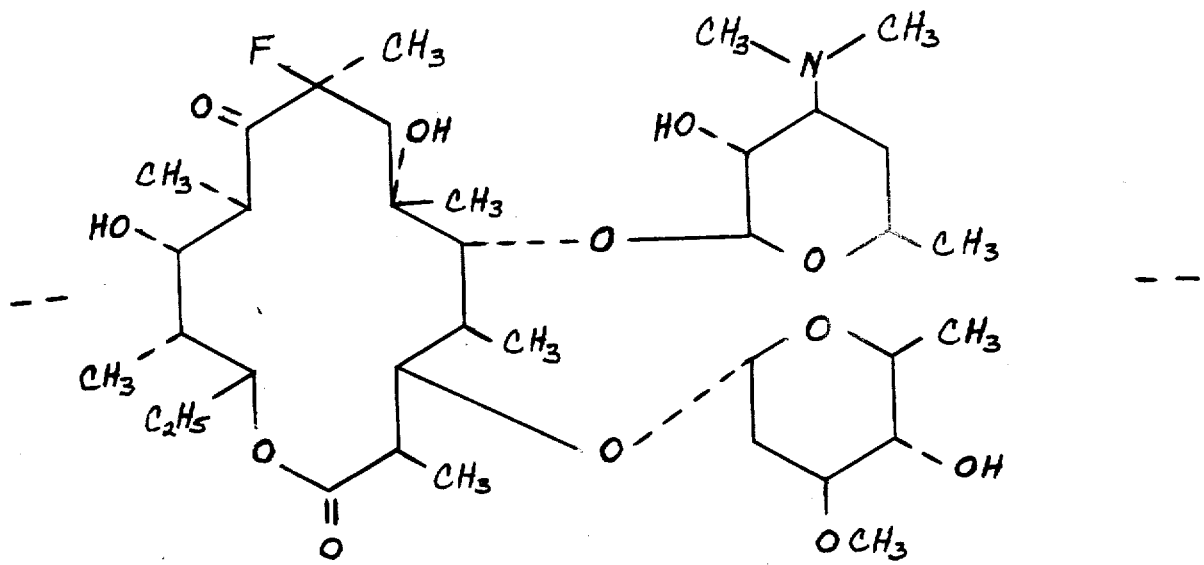

UNITED STATES PATENT AND TRADEMARK OFFICE
CERTIFICATE OF CORRECTION

PATENT NO. : 4,439,426

DATED : March 27, 1984

INVENTOR(S) : Luciano Toscano et al

It is certified that error appears in the above-identified patent and that said Letters Patent is hereby corrected as shown below:

Col. 8, line 26, delete "(8S)-8 fluoroerythronolide" and insert therefor -- (8S)-8-fluoroerythronolide -- .

Col. 11, line 32, delete "(P-80206)" and insert therefor -- (P-80205) -- ; and line 33, delete "(P-80205)" and insert therefor -- (P-80206) -- .

Col. 12, line 58, after "(shoulder)", insert -- 3250 (broad), -- ; and line 59, delete "1370" and insert therefor -- 1380 --

Col. 14, line 19, after "desosaminyl" delete "-58S)-" and insert therefor -- -(8S)- -- .

Col. 17, line 48, delete "(P-80202°" and insert therefor -- (P-80202) --

Col. 22, line 2, delete "watern" and insert therefor -- water, -- .

UNITED STATES PATENT AND TRADEMARK OFFICE
CERTIFICATE OF CORRECTION

PATENT NO. : 4,439,426  Page 9 of 11
DATED : March 27, 1984
INVENTOR(S) : Luciano Toscano et al It is certified that error appears in the above-identified patent and that said Letters Patent is hereby corrected as shown below:

Claim 4 (Col. 30), delete the structural formula in its entirety and insert therefor

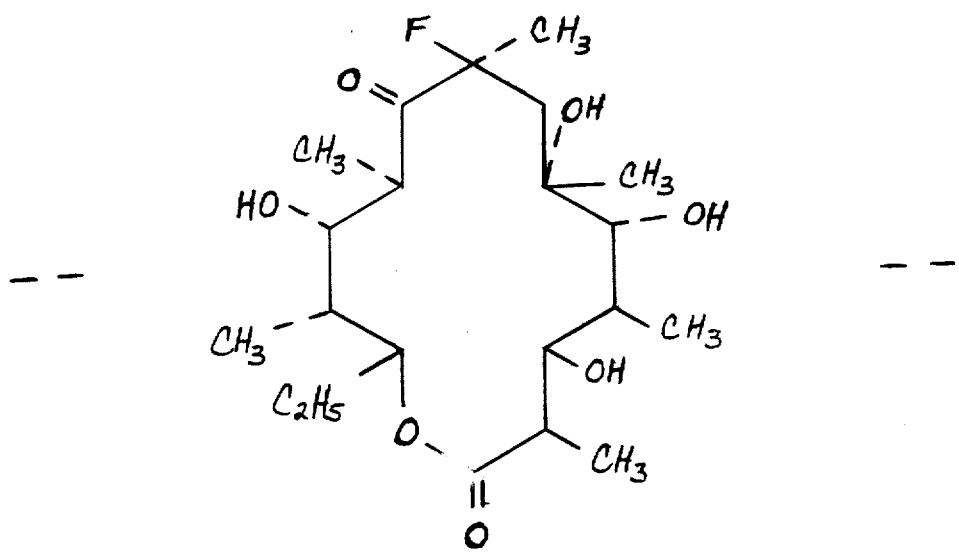

UNITED STATES PATENT AND TRADEMARK OFFICE
CERTIFICATE OF CORRECTION

PATENT NO. : 4,439,426

DATED : March 27, 1984

INVENTOR(S) : Luciano Toscano et al

It is certified that error appears in the above-identified patent and that said Letters Patent is hereby corrected as shown below:

Claim 5 (Col. 30), delete the structural formula in its entirety and insert therefor

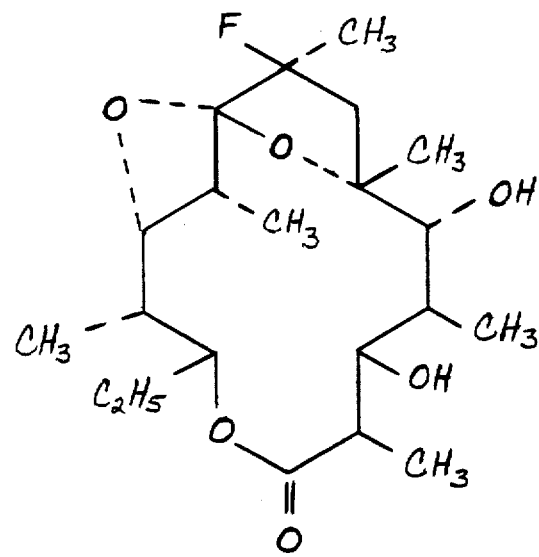

UNITED STATES PATENT AND TRADEMARK OFFICE
CERTIFICATE OF CORRECTION

PATENT NO. : 4,439,426      Page 11 of 11
DATED      : March 27, 1984
INVENTOR(S): Luciano Toscano et al It is certified that error appears in the above-identified patent and that said Letters Patent is hereby corrected as shown below:

Claim 8 (col. 31), delete the structural formula in its entirety and insert therefor

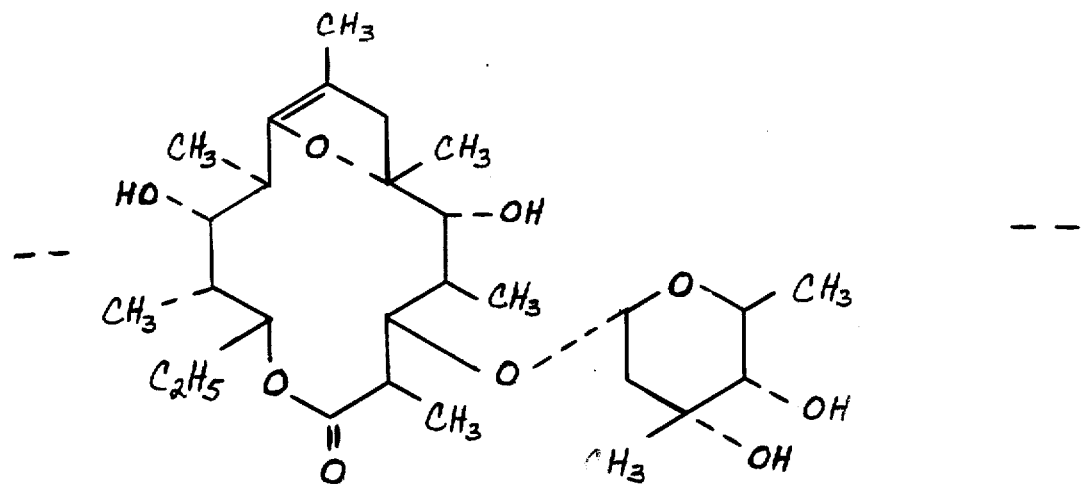

Signed and Sealed this

Eleventh Day of June 1985

[SEAL]

Attest:

DONALD J. QUIGG

Attesting Officer    Acting Commissioner of Patents and Trademarks